(12) United States Patent
Sommer et al.

(10) Patent No.: US 10,166,183 B2
(45) Date of Patent: Jan. 1, 2019

(54) PHARMACEUTICAL FORMULATIONS

(71) Applicant: AUSPEX PHARMACEUTICALS, INC., La Jolla, CA (US)

(72) Inventors: Andreas Sommer, La Jolla, CA (US); Chengzhi Zhang, La Jolla, CA (US); John Carter, La Jolla, CA (US); John Arthur, La Jolla, CA (US); Margaret Bradbury, La Jolla, CA (US)

(73) Assignee: Auspex Pharmaceuticals, Inc., La Jolla, CA (US)

( * ) Notice: Subject to any disclaimer, the term of this patent is extended or adjusted under 35 U.S.C. 154(b) by 0 days.

(21) Appl. No.: 15/116,970

(22) PCT Filed: Feb. 5, 2015

(86) PCT No.: PCT/US2015/014545
§ 371 (c)(1),
(2) Date: Aug. 5, 2016

(87) PCT Pub. No.: WO2015/120110
PCT Pub. Date: Aug. 13, 2015

(65) Prior Publication Data
US 2016/0346200 A1  Dec. 1, 2016

Related U.S. Application Data

(60) Provisional application No. 61/937,189, filed on Feb. 7, 2014, provisional application No. 61/990,061, filed on May 7, 2014.

(51) Int. Cl.
| | | |
|---|---|---|
| A61K 9/00 | (2006.01) | |
| A61K 31/522 | (2006.01) | |
| A61K 31/19 | (2006.01) | |
| A61K 31/4745 | (2006.01) | |
| A61K 31/437 | (2006.01) | |
| A61K 9/20 | (2006.01) | |
| A61K 31/00 | (2006.01) | |
| A61K 9/28 | (2006.01) | |

(52) U.S. Cl.
CPC .......... *A61K 9/0065* (2013.01); *A61K 9/2018* (2013.01); *A61K 9/2027* (2013.01); *A61K 9/2031* (2013.01); *A61K 9/2054* (2013.01); *A61K 31/19* (2013.01); *A61K 31/437* (2013.01); *A61K 31/4745* (2013.01); *A61K 31/522* (2013.01); *A61K 9/2013* (2013.01); *A61K 9/284* (2013.01); *A61K 31/00* (2013.01)

(58) Field of Classification Search
None
See application file for complete search history.

(56) References Cited

U.S. PATENT DOCUMENTS

| | | | |
|---|---|---|---|
| 2,830,993 A | 4/1958 | Brossi et al. | |
| 3,045,021 A | 7/1962 | Brossi | |
| 6,762,180 B1 | 7/2004 | Roth et al. | |
| 7,456,317 B2 | 11/2008 | Gant et al. | |
| 7,598,273 B2 | 10/2009 | Gant et al. | |
| 7,638,651 B2 | 12/2009 | Gant et al. | |
| 7,745,665 B2 | 6/2010 | Gant et al. | |
| 7,767,860 B2 | 8/2010 | Gant et al. | |
| 7,772,248 B2 | 8/2010 | Gant et al. | |
| 7,863,308 B2 | 1/2011 | Gant et al. | |
| 7,872,013 B2 | 1/2011 | Gant et al. | |
| 8,227,451 B2 | 7/2012 | Gant et al. | |
| 8,299,084 B2 | 10/2012 | Rao et al. | |
| 8,383,823 B2 | 2/2013 | Gant et al. | |
| 8,575,348 B2 | 11/2013 | Rao et al. | |
| 8,586,760 B2 | 11/2013 | Rao et al. | |
| 9,233,959 B2* | 1/2016 | Sommer | A61K 9/0065 |
| 9,296,739 B2* | 3/2016 | Sommer | A61K 9/0065 |
| 2008/0103189 A1 | 5/2008 | Gant et al. | |
| 2008/0234257 A1 | 9/2008 | Gant et al. | |
| 2008/0299204 A1 | 12/2008 | Nangia et al. | |
| 2008/0312247 A1 | 12/2008 | Gant et al. | |
| 2010/0055133 A1 | 3/2010 | Duffield et al. | |
| 2010/0120861 A1 | 5/2010 | Gant et al. | |
| 2010/0130480 A1 | 5/2010 | Gant et al. | |
| 2010/0130543 A1 | 5/2010 | Gant et al. | |
| 2011/0053866 A1* | 3/2011 | Duffield | A61K 9/0004 514/21.2 |
| 2011/0053968 A1 | 3/2011 | Zhang | |
| 2011/0117214 A1 | 5/2011 | Newbold et al. | |
| 2011/0201626 A1 | 8/2011 | Rao et al. | |
| 2011/0206661 A1 | 8/2011 | Zhang et al. | |
| 2011/0306552 A1 | 12/2011 | Rao et al. | |
| 2012/0003330 A1 | 1/2012 | Gant et al. | |
| 2012/0301458 A1 | 11/2012 | Rao et al. | |
| 2015/0004231 A1 | 1/2015 | Sommer et al. | |

FOREIGN PATENT DOCUMENTS

| | | | |
|---|---|---|---|
| EP | 1716145 A1 | 11/2006 | |
| WO | 2004/017948 A2 | 3/2004 | |
| WO | 2004/021972 A2 | 3/2004 | |
| WO | 2005/077946 A1 | 8/2005 | |
| WO | 2005/123703 A2 | 12/2005 | |

(Continued)

OTHER PUBLICATIONS

Wiebe and Knaus, Adv. Drug Delivery Rev. 1999, 39, 63-80.

(Continued)

*Primary Examiner* — Brian J Davis
(74) *Attorney, Agent, or Firm* — Baker & Hostetler LLP

(57) ABSTRACT

The present invention relates to new extended release pharmaceutical compositions and methods of use thereof for the treatment of disorders. In certain embodiments, disclosed herein is an extended-release pharmaceutical formulation comprising, in a solid dosage form for oral delivery of between about 100 mg and about 1 g total weight: between about 2 and about 18% of an active ingredient; between about 70% and about 96% of one or more diluents; between about 1% and about 10% of a water-soluble binder and between about 0.5 and about 2% of a surfactant.

21 Claims, 2 Drawing Sheets

(56) References Cited

FOREIGN PATENT DOCUMENTS

| | | | |
|---|---|---|---|
| WO | 2006/067165 A2 | 6/2006 |
| WO | 2007/093450 A2 | 8/2007 |
| WO | 2007/130365 A2 | 11/2007 |
| WO | 2008/058261 A1 | 5/2008 |
| WO | 2009/108375 A1 | 9/2009 |
| WO | 2009/108383 A2 | 9/2009 |
| WO | 2009/109993 A1 | 9/2009 |
| WO | 2009/114648 A1 | 9/2009 |
| WO | 2010/025407 A1 | 3/2010 |
| WO | 2011/123524 A2 | 10/2011 |
| WO | 2012/028635 A1 | 3/2012 |
| WO | 2012/031072 A1 | 3/2012 |
| WO | 2012/031073 A1 | 3/2012 |
| WO | 2013/159006 A1 | 10/2013 |
| WO | 2013/170242 A1 | 11/2013 |
| WO | 2013/170243 A1 | 11/2013 |
| WO | 2013/186311 A1 | 12/2013 |
| WO | 2014/047167 A1 | 3/2014 |

OTHER PUBLICATIONS

Weyler et al. (J. Biol Chem. 1985, 260, 13199-13207).
Wermuth, "The Practice of Medicinal Chemistry" Academic Press, 1996, pp. 671-691.
Wang et al., Curr. Pharm. Design 1999, 5, 265-287.
Waller et al., Br. J. Clin. Pharmac. 1989, 28, 497-507.
Uebelhack et al. (Pharmacopsychiatry, 1998, 31, 187-192).
Taylor, Adv. Drug Delivery Rev. 1996, 19, 131-148.
Tan et al., Adv. Drug Delivery Rev. 1999, 39, 117-151.
Stella et al., Drugs 1985, 29, 455-73.
Sinhababu and Thakker, Adv. Drug Delivery Rev. 1996, 19, 241-273.
Singer et al., J. Appl. Res. (2006), 6(3), 240-245.
Schwartz, et al., Biochemical Pharmacology 1966, 15(5), 645-55.
Scherman et al., Mol. Pharmacol. 1988, 33(I):72-7.
Roth et al., J. Med. Chem., 2009, 52(14), 4466-4480.
Roberts et al., Journal of Chromatography, Biomedical Applications 1981, 226(1), 175-82.
Rishel et al., J. Org. Chem., 2009, (74), 4001-4004.
Rao et al., Adv. Neurol., 1973, 3, 73-7.
Popp et al.,/. Pharm. Sci., 1978, 67 (6), 871-873.
Pinder et al., Drugs, 1976, 11(5), 329-77.
Pauletti et al., Adv. Drug. Delivery Rev. 1997, 27, 235-256.
Nathwani and Wood, Drugs 1993, 45, 866-94.
Mizen et al., Pharm. Biotech. 1998, 11, 345-365.
Mehvar, et al., Drug Metabolism and Disposition 1987, 15(2), 250-5.
Li et al. Rapid Communications in Mass Spectrometry 2005, 19, 1943-1950.
Lee et al., J. Med. Chem., 1996, (39), 191-196.
Ko et al. (British Journal of Clinical Pharmacology, 2000, 49, 343-351).
Kilbourn et al., Chirality, 1997, (9), 59-62.
Jindal, et al., Journal of Chromatography, Biomedical Applications 1989, 493(2), 392-7.
Ivanov et al., Heterocycles 2001, 55(8), 1569-1572.
Heller, "Use of Polymers in Controlled Release of Active Agents" SRI International, pp. 179-212; Downloaded by [Reprints Desk] on Jan. 12, 2017.
Harper, Progress in Drug Research 1962, 4, 221-294.
Gangwar, et al.,"Prodrug strategies to enhance the intestinal absorption of peptides" Reviews, Research focus, vol. 2, No. 4, Apr. 1997, pp. 148-154.
Asghamejad "Improving Oral Drug Transport via Prodrugs" Merck Research Laboratories, Marcel Dekker Inc. 2000, 34 Pages.
Friis and Bundgaard, Eur. J. Pharm. Sci. 1996, 4, 49-59.
Freeman et al.,/. Chem. Soc., Chem. Commun. 1991, 875-877.
Fleisher et al., Methods Enzymol. 1985, 112, 360-381.
Fleisher et al., Adv. Drug Delivery Rev. 1996, 19, 115-130.
Farquhar et al., J. Pharm. Sci. 1983, 72, 324-325.
Falck RL. Carbidopa and Levodopa an Evaluation. Drug Intelligence & Clinical Pharmacy. Feb. 1976;10(2):84-5.
DaSilva et al. Synthesis of [11C] tetrabenazine, a vesicular monoamine uptake inhibitor, for PET imaging studies. Applied Radiation and Isotopes. Apr. 1, 1993;44(4):673-676.
Pahwa et al.,Handbook of Parkinson's Disease (3rd. Edition), 2003, 36 Pages.
Danielczyk, J. Neural. Trans., Suppl., 1995, 46 (Parkinsons Disease: Experimental Models and Therapy), 399-405.
Bundgaard, Arch. Pharm. Chem. 1979, 86, 1-39.
Bundgaard, Adv. Drug Delivery Rev. 1992, 8, 1-38.
Browne, Clin. Neuropharmacol. 1997, 20, 1-12.
Boldt et al, Synthesis of (+)-and (−)-Tetrabenazine from the Resolution of a-Dihydrotetrabenazine. Synthetic Communications®. Sep. 18, 2009;39(20):3574-3585.
Berge et al., J. Pharm. Sci. 1977, 66, 1-19.
Balimane and Sinko, Adv. Drug Delivery Rev. 1999, 39, 183-209.
Balant et al., Eur. J. Drug Metab. Pharmacokinet. 1990, 15, 143-53.

* cited by examiner

Tetrabenazine Tablet Manufacturing Flow Chart

PHARMACEUTICAL FORMULATIONS

CROSS-REFERENCE TO RELATED APPLICATIONS

This application is a National Stage Application filed under 35 U.S.C. 371 of International Patent Application No. PCT/US2015/014545, filed Feb. 5, 2015, which claims the benefit of priority of U.S. Provisional Patent Application No. 61/937,189, filed Feb. 7, 2014 and No. 61/990,061, filed May 7, 2014, the disclosures of which are hereby incorporated by reference, as if written herein in its entireties.

Disclosed herein are new pharmaceutical compositions, formulations, and methods of use thereof for the treatment of disorders.

The administration of various drugs can be complicated by unfavorable pharmacodynamic and/or pharmacokinetic properties such as poor absorption or low bioavailability, short half-life or $T_{max}$, high maximal plasma concentration, low minimal plasma concentrations, or unfavorable food effects.

Thus, there is a need to develop extended release pharmaceutical formulations that provide improved drug delivery properties, such as increased half-life, increased $T_{max}$, reduced $C_{max}$ and/or dose-normalized $C_{max}$, while maintaining acceptable bioavailability and moderate food effects.

Novel pharmaceutical compositions have been discovered, together with methods of synthesizing and using the compositions, including methods for the treatment of disorders in a patient by administering the compositions as disclosed herein.

Figure 1:
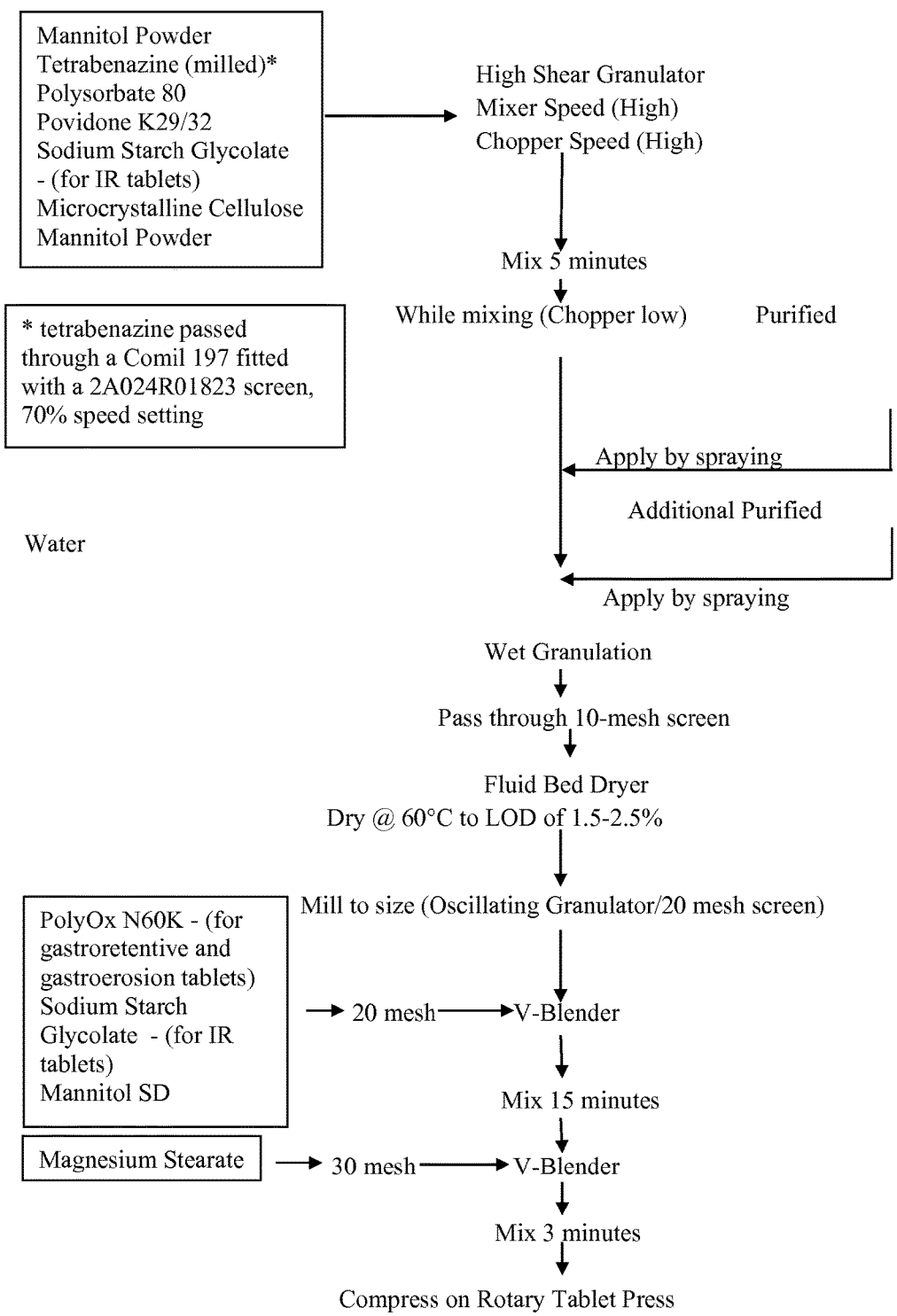
FIG. 1: Method of preparation of tetrabenazine extended release formulations.

In certain embodiments, disclosed herein is an extended-release pharmaceutical formulation comprising, in a solid dosage form for oral delivery of between about 100 mg and about 1 g total weight:
between about 2 and about 18% of an active ingredient;
between about 70% and about 96% of one or more diluents;
between about 1% and about 10% of a water-soluble binder; and
between about 0.5 and about 2% of a surfactant.

In certain embodiments, the diluent or diluents are chosen from mannitol, lactose, and microcrystalline cellulose; the binder is a polyvinylpyrrolidone; and the surfactant is a polysorbate.

In certain embodiments, the extended-release pharmaceutical formulation comprises between about 2.5% and about 11% of an active ingredient.

In certain embodiments, the extended-release pharmaceutical formulation comprises:
between about 60% and about 70% mannitol or lactose;
between about 15% and about 25% microcrystalline cellulose
about 5% of polyvinylpyrrolidone K29/32; and
between about 1 and about 2% of Tween 80.

In certain embodiments, the extended-release pharmaceutical formulation comprises:
between about 4% and about 9% of an active ingredient;
between about 60% and about 70% mannitol or lactose;
between about 20% and about 25% microcrystalline cellulose
about 5% of polyvinylpyrrolidone K29/32; and
about 1.4% of Tween 80.

In certain embodiments, disclosed herein is an extended-release pharmaceutical formulation comprising, in a solid dosage form for oral delivery of between about 100 mg and about 1 g total weight:
between about 70 and about 95% of a granulation of an active ingredient, wherein the active ingredient comprises between about 1 and about 15% of the granulation;
between about 5% and about 15% of one or more diluents;
between about 5% and about 20% of sustained-release polymer; and
between about 0.5 and about 2% of a lubricant.

In certain embodiments, the extended-release pharmaceutical formulation comprises:
between about 5% and about 15% of one or more spray-dried mannitol or spray-dried lactose;
between about 5% and about 20% of sustained-release polymer; and
between about 0.5 and about 2% of a magnesium stearate.

In certain embodiments, the sustained-release polymer is chosen from a polyvinyl acetate-polyvinylpyrrolidone mixture and a poly(ethylene oxide) polymer.

In certain embodiments, the sustained-release polymer is chosen from Kollidon® SR, POLYOX® N60K, and Carbopol®.

In certain embodiments, the sustained-release polymer is Kollidon® SR.

In certain embodiments, the sustained-release polymer is POLYOX® N60K.

In certain embodiments, the sustained-release polymer is Carbopol®.

In certain embodiments, the extended-release pharmaceutical formulation comprises from about 5 mg to about 250 mg of an active ingredient.

In certain embodiments, the active ingredient is selected from the group consisting of tetrabenazine, dihydrotetrabenazine, ketamine, pirfenidone, phenylephrine, ethambutol, venlafaxine, zolipidem, esomeprazole, lansoprazole, omeprazole, pantoprazole, rabeprazole, sitaxentan, codeine, hydrocodone, morphine, oxycodone, almotriptan, eletriptan, naratriptan, sumatriptan, zolmitriptan, ranolazine, desmethylvenlafaxine, mirabegron, ticagrelor, darapladib, rilapladib, nilotinib, tofacitinib, apixaban, lumiracoxib, solabegron, riociguat, cariprazine, neratinib, pelitinib, fostamatinib, R-406, dihydrotetrabenazine, NBI-98854, nintedanib, F-351, agomelatine, almorexant, alogliptin, anastrozole, aripiprazole, atomoxetine, bosentan, brivaracetam, bupropion, cediranib, cinacalcet, clemizole, dextromethorphan, dimeboline, donepezil, duloxetine, fingolimod, gefitinib, imatinib, ITMN-191, ivabradine, linezolid, lonafarnib, maraviroc, mosapride, nateglinide, oxybutynin, paroxetine, pazopanib, quetiapine, rilpivirine, rimonabant, rolofylline, sitagliptin, tolterodine, udenafil, valproic acid, vandetanib, vildagliptin, alpha-lipoic acid, ambrisentan, anacetrapib, apremilast, atazanavir, bardoxolone, baricitinib, boceprevir, brecanavir, carfilzomib, carmofur, cilostazol, conivaptan, crizotinib, darunavir, dasatinib, dimethylcurcumin, dolutegravir, elvitegravir, erlotinib, etravirine, felbamate, filibuvir, gliclazide, ibudilast, ibrutinib, idebenone, iloperidone, iloprost, indiplon, ivacaftor, L-838417, lacosamide, lapatinib, lenalidomide, lorcaserin, mibefradil, milnacipran, N-butyl bumetanide, NTP-2014, niacin, niacin prodrugs, NS11394, NS-304, MRE-304, MRE-269, pagoclone, pentifylline, pentoxifylline, pentoxifylline metabolites, PLX4032, pomalidomide, ponatinib, PPL-100, praziquantel, preladenant, primaquine, radequinil, raltegravir, rigosertib, rivaroxaban, ruxolitinib, safinamide, silodosin, sodium oxybate, 4-hydroxybutyrate, sorafenib, telcagepant, thalidomide, tigecycline, omadacycline, tizanidine, TPA-023, treprostinil, varespladib, vercirnon, vicriviroc, levodopa, carbidopa, levodopa in combination with carbidopa, amantadine, dipraglurant, nintedanib, and pridopidine.

In certain embodiments, the active ingredient is selected from the group consisting of a deuterated analog of tetrabenazine, a deuterated analog of dihydrotetrabenazine, a deuterated analog of ketamine, a deuterated analog of pirfenidone, a deuterated analog of phenylephrine, a deuterated analog of ethambutol, a deuterated analog of venlafaxine, a deuterated analog of zolipidem, a deuterated analog of esomeprazole, a deuterated analog of lansoprazole, a deuterated analog of omeprazole, a deuterated analog of pantoprazole, a deuterated analog of rabeprazole, a deuterated analog of sitaxentan, a deuterated analog of codeine, a deuterated analog of hydrocodone, a deuterated analog of morphine, a deuterated analog of oxycodone, a deuterated analog of almotriptan, a deuterated analog of eletriptan, a deuterated analog of naratriptan, a deuterated analog of sumatriptan, a deuterated analog of zolmitriptan, a deuterated analog of ranolazine, a deuterated analog of desmethylvenlafaxine, a deuterated analog of mirabegron, a deuterated analog of ticagrelor, a deuterated analog of darapladib, a deuterated analog of rilapladib, a deuterated analog of nilotinib, a deuterated analog of tofacitinib, a deuterated analog of apixaban, a deuterated analog of lumiracoxib, a deuterated analog of solabegron, a deuterated analog of riociguat, a deuterated analog of cariprazine, a deuterated analog of neratinib, a deuterated analog of pelitinib, a deuterated analog of fostamatinib, a deuterated analog of R-406, a deuterated analog of dihydrotetrabenazine, a deuterated analog of NBI-98854, a deuterated analog of nintedanib, a deuterated analog of F-351, a deuterated analog of agomelatine, a deuterated analog of almorexant, a deuterated analog of alogliptin, a deuterated analog of anastrozole, a deuterated analog of aripiprazole, a deuterated analog of atomoxetine, a deuterated analog of bosentan, a deuterated analog of brivaracetam, a deuterated analog of bupropion, a deuterated analog of cediranib, a deuterated analog of cinacalcet, a deuterated analog of clemizole, a deuterated analog of dextromethorphan, a deuterated analog of dimeboline, a deuterated analog of donepezil, a deuterated analog of duloxetine, a deuterated analog of fingolimod, a deuterated analog of gefitinib, a deuterated analog of imatinib, a deuterated analog of ITMN-191, a deuterated analog of ivabradine, a deuterated analog of linezolid, a deuterated analog of lonafarnib, a deuterated analog of maraviroc, a deuterated analog of mosapride, a deuterated analog of nateglinide, a deuterated analog of oxybutynin, a deuterated analog of paroxetine, a deuterated analog of pazopanib, a deuterated analog of quetiapine, a deuterated analog of rilpivirine, a deuterated analog of rimonabant, a deuterated analog of rolofylline, a deuterated analog of sitagliptin, a deuterated analog of tolterodine, a deuterated analog of udenafil, a deuterated analog of valproic acid, a deuterated analog of vandetanib, a deuterated analog of vildagliptin, a deuterated analog of alpha-lipoic acid, a deuterated analog of ambrisentan, a deuterated analog of anacetrapib, a deuterated analog of apremilast, a deuterated analog of atazanavir, a deuterated analog of bardoxolone, a deuterated analog of baricitinib, a deuterated analog of boceprevir, a deuterated analog of brecanavir, a deuterated analog of carfilzomib, a deuterated analog of carmofur, a deuterated analog of cilostazol, a deuterated analog of conivaptan, a deuterated analog of crizotinib, a deuterated analog of darunavir, a deuterated analog of dasatinib, a deuterated analog of dimethylcurcumin, a deuterated analog of dolutegravir, a deuterated analog of elvitegravir, a deuterated analog of erlotinib, a deuterated analog of etravirine, a deuterated analog of felbamate, a deuterated analog of filibuvir, a deuterated analog of gliclazide, a deuterated analog of ibudilast, a deuterated analog of ibrutinib, a deuterated analog of idebenone, a deuterated analog of iloperidone, a deuterated analog of iloprost, a deuterated analog of indiplon, a deuterated analog of ivacaftor, a deuterated analog of L-838417, a deuterated analog of lacosamide, a deuterated analog of lapatinib, a deuterated analog of lenalidomide, a deuterated analog of lorcaserin, a deuterated analog of mibefradil, a deuterated analog of milnacipran, a deuterated analog of N-butyl bumetanide, a deuterated analog of NTP-2014, a deuterated analog of niacin, a deuterated analog of niacin prodrugs, a deuterated analog of NS11394, a deuterated analog of NS-304, a deuterated analog of MRE-304, a deuterated analog of MRE-269, a deuterated analog of pagoclone, a deuterated analog of pentifylline, a deuterated analog of pentoxifylline, a deuterated analog of pentoxifylline metabolites, a deuterated analog of PLX4032, a deuterated analog of pomalidomide, a deuterated analog of ponatinib, a deuterated analog of PPL-100, a deuterated analog of praziquantel, a deuterated analog of preladenant, a deuterated analog of primaquine, a deuterated analog of radequinil, a deuterated analog of raltegravir, a deuterated analog of rigosertib, a deuterated analog of rivaroxaban, a deuterated analog of ruxolitinib, a deuterated analog of safinamide, a deuterated analog of silodosin, a deuterated analog of sodium oxybate, a deuterated analog of 4-hydroxybutyrate, a deuterated analog of sorafenib, a deuterated analog of telcagepant, a deuterated analog of thalidomide, a deuterated analog of tigecycline, a deuterated analog of omadacycline, a deuterated analog of tizanidine, a deuterated analog of TPA-023, a deuterated analog of treprostinil, a deuterated analog of varespladib, a deuterated analog of vercirnon, a deuterated analog of vicriviroc, a deuterated analog of levodopa, a deuterated analog of carbidopa, a deuterated analog of levodopa in combination with a deuterated analog of carbidopa, a deuterated analog of amantadine, a deuterated analog of dipraglurant, a deuterated analog of nintedanib, a deuterated analog of pridopidine, CTP-354, CTP-499, AVP-786, JZP-386, and CTP-730.

In certain embodiments, the active ingredient is

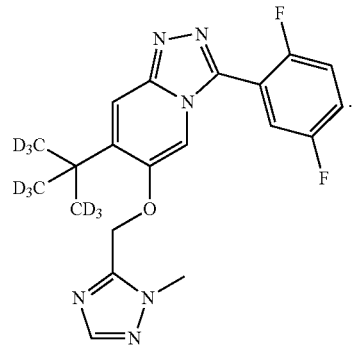 [SMILES: [2H]C([2H])([2H])C(c1cc2nnc(-c3cc(F)ccc3F)n2cc1OCc1ncnn1C)(C([2H])([2H])[2H])C([2H])([2H])[2H]]

In certain embodiments, the active ingredient is

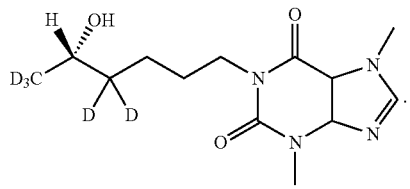 [SMILES: [2H]C([2H])([2H])[C@H](O)C([2H])([2H])CCCN1C(=O)C2C(N=CN2C)N(C)C1=O]

In certain embodiments, the active ingredient is

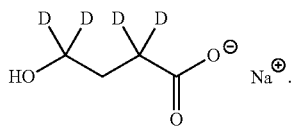 [SMILES: [2H]C([2H])(O)CC([2H])([2H])C(=O)[O-] ; [Na+]]

In certain embodiments, the active ingredient is selected from the group consisting of tetrabenazine, dihydrotetrabenazine, ketamine, a deuterated analog of ketamine, pirfenidone, and a deuterated analog of pirfenidone.

In certain embodiments, the active ingredient is ketamine.

In certain embodiments, the active ingredient is a deuterated analog of pirfenidone.

In certain embodiments, the active ingredient is pirfenidone.

In certain embodiments, the active ingredient is a deuterated analog of pirfenidone.

In certain embodiments, disclosed herein is a method of treating a disease comprising the administration of the extended release pharmaceutical composition as recited in claim 1, wherein the dose-normalized $C_{max}$ of the active ingredient resulting from the administration of the extended-release formulation is lower than the dose-normalized $C_{max}$ resulting from the administration of the immediate release formulated or unformulated active ingredient.

In certain embodiments, the ratio of extended release formulated $C_{max}$ to immediate release formulated or unformulated $C_{max}$ is less than 1.

In certain embodiments, the ratio of extended release formulated $C_{max}$ to immediate release formulated or unformulated $C_{max}$ is less than about 0.9.

In certain embodiments, the ratio of extended release formulated $C_{max}$ to immediate release formulated or unformulated $C_{max}$ is less than about 0.8.

In certain embodiments, the ratio of extended release formulated $C_{max}$ to immediate release formulated or unformulated $C_{max}$ is less than about 0.7.

In certain embodiments, the ratio of extended release formulated $C_{max}$ to immediate release formulated or unformulated $C_{max}$ is less than about 0.5.

In certain embodiments, disclosed herein is a method of treating a disease comprising the administration of the extended release pharmaceutical composition as recited in claim 1, wherein the $T_{max}$ of the active ingredient resulting from the administration of the extended-release formulation occurs later than the $T_{max}$ resulting from the administration of the immediate release formulated or unformulated active ingredient.

In certain embodiments, the ratio of immediate release formulated or unformulated $T_{max}$ to extended release formulated $T_{max}$ is less than 1.

In certain embodiments, the ratio of immediate release formulated or unformulated $T_{max}$ to extended release formulated $T_{max}$ is less than about 0.75.

In certain embodiments, the ratio of immediate release formulated or unformulated $T_{max}$ to extended release formulated $T_{max}$ is less than about 0.5.

In certain embodiments, the ratio of immediate release formulated or unformulated $T_{max}$ to extended release formulated $T_{max}$ is less than about 0.25.

In certain embodiments, disclosed herein is a method of treating a disease comprising the administration of the extended release pharmaceutical composition as recited in claim 1 with food, wherein the ratio of fed to fasted $C_{max}$ of the total combined amount of the active ingredient is greater than 1.

In certain embodiments, the ratio of fed to fasted $C_{max}$ is greater than about 1.5.

In certain embodiments, the ratio of fed to fasted $C_{max}$ is greater than about 2.0.

In certain embodiments, disclosed herein is a method of treating a disease comprising the administration of the extended release pharmaceutical composition as recited in claim 1, wherein the ratio of fed to fasted $AUC_{inf}$ of the active ingredient is greater than 1.

In certain embodiments, the ratio of fed to fasted $AUC_{inf}$ is greater than about 1.1.

In certain embodiments, the ratio of fed to fasted $AUC_{inf}$ is greater than about 1.2.

In certain embodiments, disclosed herein is a method of treating a VMAT2-mediated disease comprising the administration of the extended release pharmaceutical composition as recited in claim 1 with food, wherein the ratio of fed to fasted $AUC_t$ of the active ingredient is greater than 1.

In certain embodiments, the ratio of fed to fasted $AUC_t$ is greater than about 1.1.

In certain embodiments, the ratio of fed to fasted $AUC_t$ is greater than about 1.2.

In certain embodiments, disclosed herein is an extended-release pharmaceutical formulation comprising, in a solid dosage form for oral delivery of between about 100 mg and about 1 g total weight:
 between about 2 and about 18% of tetrabenazine or dihydrotetrabenazine;
 between about 70% and about 96% of one or more diluents;
 between about 1% and about 10% of a water-soluble binder; and
 between about 0.5 and about 2% of a surfactant.

In certain embodiments, the total weight is about 350 mg and about 750 mg.

In certain embodiments, the diluent or diluents are chosen from mannitol, lactose, and microcrystalline cellulose;
 the binder is a polyvinylpyrrolidone; and
 the surfactant is a polysorbate.

In certain embodiments, the extended-release pharmaceutical formulation comprises between about 2.5% and about 11% of tetrabenazine or dihydrotetrabenazine.

In certain embodiments, the extended-release pharmaceutical formulation comprises:
 between about 60% and about 70% mannitol or lactose;
 between about 15% and about 25% microcrystalline cellulose
 about 5% of polyvinylpyrrolidone K29/32; and
 between about 1 and about 2% of Tween 80.

In certain embodiments, the extended-release pharmaceutical formulation comprises:
 between about 4% and about 9% of a tetrabenazine or dihydrotetrabenazine;
 between about 60% and about 70% mannitol or lactose;
 between about 20% and about 25% microcrystalline cellulose
 about 5% of polyvinylpyrrolidone K29/32; and
 about 1.4% of Tween 80.

In certain embodiments, the extended-release pharmaceutical formulation comprises about 7.5, 12.5 mg, 15 mg, 25 mg, 30 mg, and 50 mg of tetrabenazine or dihydrotetrabenazine.

In certain embodiments, the extended-release pharmaceutical formulation comprises, in a solid dosage form for oral delivery of between about 100 mg and about 1 g total weight:

between about 70 and about 95% of a granulation of tetrabenazine or dihydrotetrabenazine, wherein the tetrabenazine or dihydrotetrabenazine comprises between about 1 and about 15% of the granulation;

between about 5% and about 15% of one or more diluents;

between about 5% and about 20% of sustained-release polymer; and between about 0.5 and about 2% of a lubricant.

In certain embodiments, the extended-release pharmaceutical formulation comprises:

between about 5% and about 15% of one or more spray-dried mannitol or spray-dried lactose;

between about 5% and about 20% of sustained-release polymer; and between about 0.5 and about 2% of a magnesium stearate.

In certain embodiments, the sustained-release polymer is chosen from a polyvinyl acetate-polyvinylpyrrolidone mixture and a poly(ethylene oxide) polymer.

In certain embodiments, the sustained-release polymer is chosen from Kollidon® SR, POLYOX® N60K, and Carbopol®.

In certain embodiments, the sustained-release polymer is Kollidon® SR.

In certain embodiments, the sustained-release polymer is POLYOX® N60K.

In certain embodiments, the sustained-release polymer is Carbopol®.

In certain embodiments, the total weight is about 350 mg and about 700 mg.

In certain embodiments, the extended-release pharmaceutical formulation comprises from about 5 mg to about 30 mg of tetrabenazine or dihydrotetrabenazine.

In certain embodiments, the extended-release pharmaceutical formulation comprises about 7.5 mg of tetrabenazine or dihydrotetrabenazine.

In certain embodiments, the extended-release pharmaceutical formulation comprises about 12.5 mg of tetrabenazine or dihydrotetrabenazine.

In certain embodiments, the extended-release pharmaceutical formulation comprises about 15 mg of tetrabenazine or dihydrotetrabenazine.

In certain embodiments, the extended-release pharmaceutical formulation comprises about 25 mg tetrabenazine or dihydrotetrabenazine.

In certain embodiments, the extended-release pharmaceutical formulation comprises about 30 mg of tetrabenazine or dihydrotetrabenazine.

In certain embodiments, the extended-release pharmaceutical formulation comprises about 50 mg of tetrabenazine or dihydrotetrabenazine.

In certain embodiments, disclosed herein is a method of treating a VMAT2-mediated disease comprising the administration of an extended release pharmaceutical composition comprising tetrabenazine or dihydrotetrabenazine with food, wherein the ratio of fed to fasted $C_{max}$ of the total combined amount of dihydrotetrabenazine is greater than 1.

In certain embodiments, disclosed herein is an extended release pharmaceutical composition comprising tetrabenazine or dihydrotetrabenazine for use in treatment of a VMAT2-mediated disease wherein the pharmaceutical composition is administered with food and the ratio of fed to fasted $C_{max}$ of the total combined amount of dihydrotetrabenazine is greater than 1.

In certain embodiments, disclosed herein is an extended release pharmaceutical composition comprising tetrabenazine or dihydrotetrabenazine for use in the manufacture of a medicament to treat a VMAT2-mediated disease wherein the pharmaceutical composition is administered with food and the ratio of fed to fasted $C_{max}$ of the total combined amount of dihydrotetrabenazine is greater than 1.

In certain embodiments, the ratio of fed to fasted $C_{max}$ is greater than about 1.4.

In certain embodiments, the ratio of fed to fasted $C_{max}$ is greater than about 1.9.

In certain embodiments, disclosed herein is a method of treating a VMAT2-mediated disease comprising the administration of an extended release pharmaceutical composition comprising tetrabenazine or dihydrotetrabenazine with food, wherein the ratio of fed to fasted $AUC_{inf}$ of the total combined amount of dihydrotetrabenazine is greater than 1.

In certain embodiments, disclosed herein is an extended release pharmaceutical composition comprising tetrabenazine or dihydrotetrabenazine for use in treatment of a VMAT2-mediated disease wherein the pharmaceutical composition is administered with food and the ratio of fed to fasted $AUC_{inf}$ of the total combined amount of dihydrotetrabenazine is greater than 1.

In certain embodiments, disclosed herein is an extended release pharmaceutical composition comprising tetrabenazine or dihydrotetrabenazine for use in the manufacture of a medicament to treat a VMAT2-mediated disease wherein the pharmaceutical composition is administered with food and the ratio of fed to fasted $AUC_{inf}$ of the total combined amount of dihydrotetrabenazine is greater than 1.

In certain embodiments, the ratio of fed to fasted $AUC_{inf}$ is greater than about 1.1.

In certain embodiments, the ratio of fed to fasted $AUC_{inf}$ is greater than about 1.2.

In certain embodiments, disclosed herein is a method of treating a VMAT2-mediated disease comprising the administration of an extended release pharmaceutical composition comprising tetrabenazine or dihydrotetrabenazine with food, wherein the ratio of fed to fasted $AUC_t$ of the total combined amount of dihydrotetrabenazine is greater than 1.

In certain embodiments, disclosed herein is an extended release pharmaceutical composition comprising tetrabenazine or dihydrotetrabenazine for use in treatment of a VMAT2-mediated disease wherein the pharmaceutical composition is administered with food and the ratio of fed to fasted $AUC_t$ of the total combined amount of dihydrotetrabenazine is greater than 1.

In certain embodiments, disclosed herein is an extended release pharmaceutical composition comprising tetrabenazine or dihydrotetrabenazine for use in the manufacture of a medicament to treat a VMAT2-mediated disease wherein the pharmaceutical composition is administered with food and the ratio of fed to fasted $AUC_t$ of the total combined amount of dihydrotetrabenazine is greater than 1.

In certain embodiments, the ratio of fed to fasted $AUC_t$ is greater than about 1.1.

In certain embodiments, the ratio of fed to fasted $AUC_t$ is greater than about 1.2.

In certain embodiments, the VMAT2-mediated disorder is a chronic hyperkinetic movement disorder.

In certain embodiments, the VMAT2-mediated disorder is selected from the group consisting of chronic hyperkinetic movement disorders, Huntington's disease, hemiballismus, chorea associated with Huntington's disease, senile chorea, tic disorders, tardive dyskinesia, dystonia, Tourette's syndrome, depression, cancer, rheumatoid arthritis, psychosis, multiple sclerosis, asthma, Parkinson's disease levodopa-induced dyskinesia, movement disorders, and oppositional defiant disorder.

In certain embodiments, the VMAT2-mediated disorder is Huntington's disease.

In certain embodiments, the VMAT2-mediated disorder is hemiballismus.

In certain embodiments, the VMAT2-mediated disorder is chorea associated with Huntington's disease.

In certain embodiments, the VMAT2-mediated disorder is senile chorea.

In certain embodiments, the VMAT2-mediated disorder is a tic disorder.

In certain embodiments, the VMAT2-mediated disorder is tardive dyskinesia.

In certain embodiments, the VMAT2-mediated disorder is dystonia.

In certain embodiments, the VMAT2-mediated disorder is Tourette's syndrome.

In certain embodiments, the VMAT2-mediated disorder is depression.

In certain embodiments, the VMAT2-mediated disorder is cancer.

In certain embodiments, the VMAT2-mediated disorder is rheumatoid arthritis.

In certain embodiments, the VMAT2-mediated disorder is psychosis.

In certain embodiments, the VMAT2-mediated disorder is multiple sclerosis.

In certain embodiments, the VMAT2-mediated disorder is asthma.

In certain embodiments, the VMAT2-mediated disorder is Parkinson's disease levodopa-induced dyskinesia.

In certain embodiments, the VMAT2-mediated disorder is levodopa-induced dyskinesia.

In certain embodiments, the VMAT2-mediated disorder is oppositional defiant disorder.

In certain embodiments of the present invention, compositions disclosed herein comprise the compound:

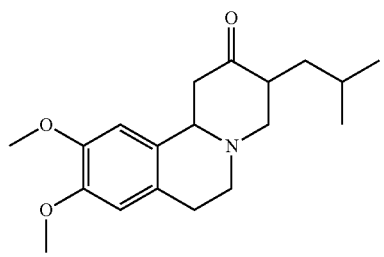 [SMILES: COc1cc2c(cc1OC)C1CC(=O)C(CC(C)C)CN1CC2]

In certain embodiments of the present invention, compositions disclosed herein comprise the compound:

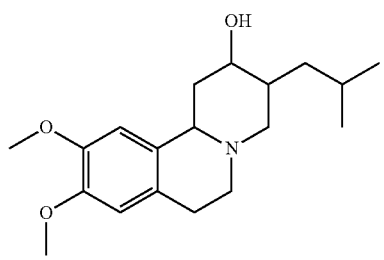 [SMILES: COc1cc2c(cc1OC)C1CC(O)C(CC(C)C)CN1CC2]

In certain embodiments of the present invention, compositions disclosed herein comprise one or more of the following compounds:

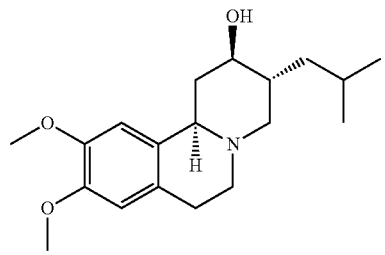

(+)-α-HTBZ

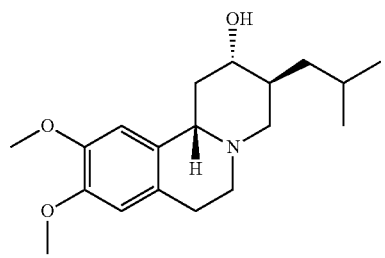

(-)-α-HTBZ

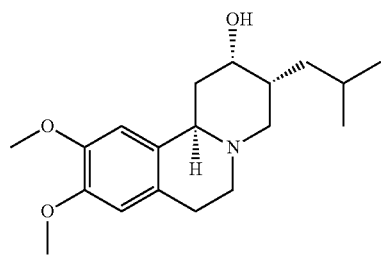

(+)-β-HTBZ

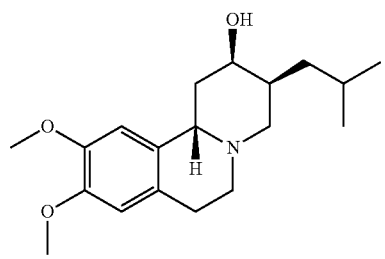

(-)-β-HTBZ

In certain embodiments of the present invention, compositions disclosed herein comprise one or more of the following compounds:

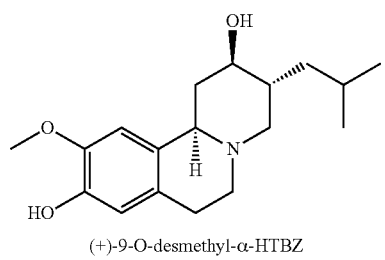

(+)-9-O-desmethyl-α-HTBZ

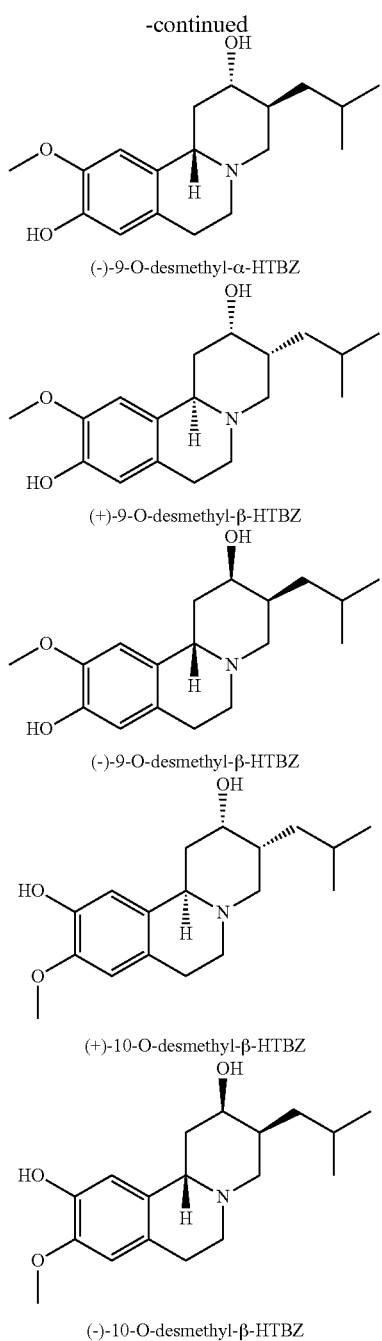

(-)-9-O-desmethyl-α-HTBZ (+)-9-O-desmethyl-β-HTBZ (-)-9-O-desmethyl-β-HTBZ (+)-10-O-desmethyl-β-HTBZ (-)-10-O-desmethyl-β-HTBZ Certain compounds disclosed herein may possess useful VMAT2 inhibiting activity, and may be used in the treatment or prophylaxis of a disorder in which VMAT2 plays an active role. Thus, certain embodiments also provide pharmaceutical compositions comprising one or more compounds disclosed herein together with a pharmaceutically acceptable carrier, as well as methods of making and using the compounds and compositions. Certain embodiments provide methods for inhibiting VMAT2. Other embodiments provide methods for treating a VMAT2-mediated disorder in a patient in need of such treatment, comprising administering to said patient a therapeutically effective amount of a compound or composition according to the present invention. Also provided is the use of certain compounds disclosed herein for use in the manufacture of a medicament for the prevention or treatment of a disorder ameliorated by the inhibition of VMAT2.

The compounds as disclosed herein may also contain less prevalent isotopes for other elements, including, but not limited to, $^{13}C$ or $^{14}C$ for carbon, $^{33}S$, $^{34}S$, or $^{36}S$ for sulfur, $^{15}N$ for nitrogen, and $^{17}O$ or $^{18}O$ for oxygen.

All publications and references cited herein are expressly incorporated herein by reference in their entirety. However, with respect to any similar or identical terms found in both the incorporated publications or references and those explicitly put forth or defined in this document, then those terms definitions or meanings explicitly put forth in this document shall control in all respects.

Tetrabenazine ((+/−)-cis-tetrabenazine, Nitoman®, Xenazine®, Tetmodis, Ro 1-9569), is a racemic mixture of (3R,11bR)-1,3,4,6,7,11b-Hexahydro-9,10-dimethoxy-3-(2-methylpropyl)-2H-benzo[a]quinolizin-2-one, and (3S,11bS)-1,3,4,6,7,11b-hexahydro-9,10-dimethoxy-3-(2-methylpropyl)-2H-benzo[a]quinolizin-2-one. Tetrabenazine is a vesicular monoamine transporter 2 (VMAT2) inhibitor. Tetrabenazine is commonly prescribed for the treatment of chorea associated with Huntington's disease (Savani et al., *Neurology* 2007, 68(10), 797; and Kenney et al., *Expert Review of Neurotherapeutics* 2006, 6(1), 7-17).

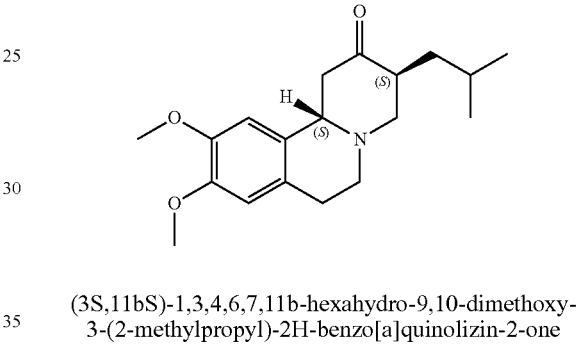

(3S,11bS)-1,3,4,6,7,11b-hexahydro-9,10-dimethoxy-3-(2-methylpropyl)-2H-benzo[a]quinolizin-2-one

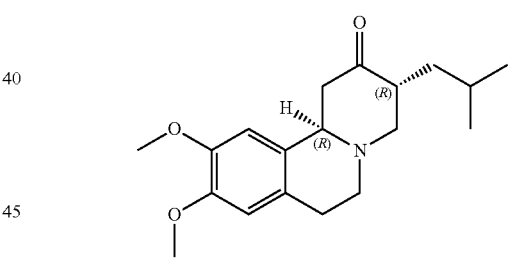

(3R,11bR)-1,3,4,6,7,11b-hexahydro-9,10-dimethoxy-3-(2-methylpropyl)-2H-benzo[a]quinolizin-2-one Tetrabenazine and its major metabolites alpha-dihydrotetrabenazine (α-HTBZ) and beta-dihydrotetrabenazine (β-HTBZ) are selective and potent inhibitors of the VMAT2. Scherman et al., *Mol. Pharmacol.* 1988, 33(1):72-7. In humans, extensive hepatic metabolism of tetrabenazine to α-HTBZ and β-HTBZ by carbonyl reductase results in plasma concentrations of tetrabenazine that are very low and are often below the limit of detection. Thus, α-HTBZ and β-HTBZ are thought to confer the pharmacological and therapeutic activity of orally administered tetrabenazine in patients. In human plasma, α-HTBZ and β-HTBZ have half-lives of 7 hours and 5 hours, respectively (Xenazine® US Prescribing Information). Alpha(α)-HTBZ and β-HTBZ are each metabolized into pairs of mono-O-desmethyl metabolites (9-O-desmethyl-HTBZ and 10-O-desmethyl-HTBZ) which are, in turn, conjugated by sulfonation and/or glucuronidation for excretion. The 9-O-desmethyl-β-HTBZ metabolite, which is derived from β-HTBZ, is also a major circulating metabolite. CYP2D6 is primarily responsible for O-demethylation of α-HTBZ and β-HTBZ in humans.

As used herein, the terms below have the meanings indicated.

The singular forms "a," "an," and "the" may refer to plural articles unless specifically stated otherwise.

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

When ranges of values are disclosed, and the notation "from $n_1$ . . . to $n_2$" or "$n_1$-$n_2$" is used, where $n_1$ and $n_2$ are the numbers, then unless otherwise specified, this notation is intended to include the numbers themselves and the range between them. This range may be integral or continuous between and including the end values.

The terms "tetrabenazine" and "(+/−)-cis-tetrabenazine" refer to a racemic mixture of (3R,11bR)-1,3,4,6,7,11b-hexahydro-9,10-di(methoxy)-3-(2-methylpropyl)-2H-benzo[a]quinolizin-2-one and (3S,11bS)-1,3,4,6,7,11b-hexahydro-9,10-di(methoxy)-3-(2-methylpropyl)-2H-benzo[a]quinolizin-2-one, which have the following structures:

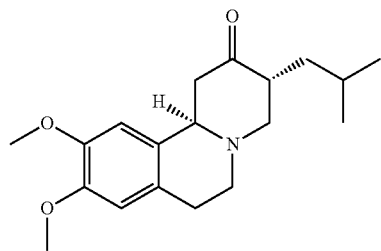 [SMILES: COc1cc2c(cc1OC)[C@H]1CC(=O)[C@H](CC(C)C)CN1CC2]

(3R,11bR)-1,3,4,6,7,11b-hexahydro-9,10-di(methoxy)-3-(2-methylpropyl)-2H-benzo[a]quinolizin-2-one

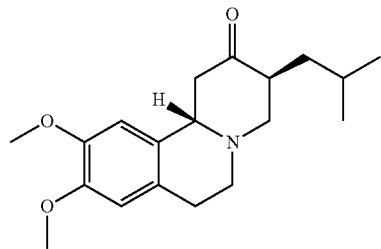 [SMILES: COc1cc2c(cc1OC)[C@@H]1CC(=O)[C@@H](CC(C)C)CN1CC2]

(3 S,11bS)-1,3,4,6,7,11b-hexahydro-9,10-di(methoxy)-3-(2-methylpropyl)-2H-benzo[a]quinolizin-2-one The term "(+/−)-trans-tetrabenazine" refers to a racemic mixture of (3R,11bS)-1,3,4,6,7,11b-hexahydro-9,10-di(methoxy)-3-(2-methylpropyl)-2H-benzo[a]quinolizin-2-one and (3S,11bR)-1,3,4,6,7,11b-hexahydro-9,10-di(methoxy)-3-(2-methylpropyl)-2H-benzo[a]quinolizin-2-one, which have the following structures:

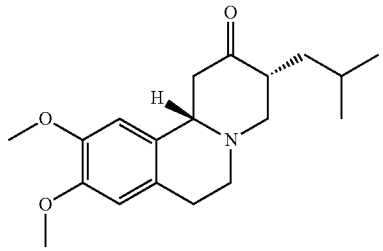 [SMILES: COc1cc2c(cc1OC)[C@@H]1CC(=O)[C@H](CC(C)C)CN1CC2]

(3R,11bS)-1,3,4,6,7,11b-hexahydro-9,10-di(methoxy)-3-(2-methylpropyl)-2H-benzo[a]quinolizin-2-one

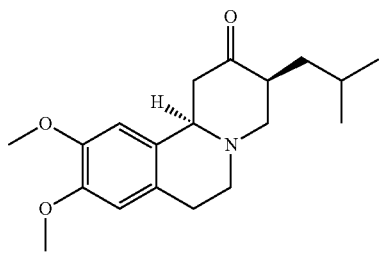 [SMILES: COc1cc2c(cc1OC)[C@H]1CC(=O)[C@@H](CC(C)C)CN1CC2]

(3 S,11bR)-1,3,4,6,7,11b-hexahydro-9,10-di(methoxy)-3-(2-methylpropyl)-2H-benzo[a]quinolizin-2-one Asymmetric centers exist in the compounds disclosed herein. These centers are designated by the symbols "R" or "S," depending on the configuration of substituents around the chiral carbon atom. It should be understood that the invention encompasses all stereochemical isomeric forms, including diastereomeric, enantiomeric, and epimeric forms, as well as D-isomers and L-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present invention includes all cis, trans, syn, anti, entgegen (E), and zusammen (Z) isomers as well as the appropriate mixtures thereof. Additionally, compounds may exist as tautomers; all tautomeric isomers are provided by this invention. Additionally, the compounds disclosed herein can exist in unsolvated as well as solvated forms with pharmaceutically acceptable solvents such as water, ethanol, and the like. In general, the solvated forms are considered equivalent to the unsolvated forms.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

The term "disorder" as used herein is intended to be generally synonymous, and is used interchangeably with, the terms "disease", "syndrome", and "condition" (as in medical condition), in that all reflect an abnormal condition of the human or animal body or of one of its parts that impairs normal functioning, is typically manifested by distinguishing signs and symptoms.

The terms "treat," "treating," and "treatment" are meant to include alleviating or abrogating a disorder or one or more of the symptoms associated with a disorder; or alleviating or eradicating the cause(s) of the disorder itself. As used herein, reference to "treatment" of a disorder is intended to include prevention. The terms "prevent," "preventing," and "prevention" refer to a method of delaying or precluding the onset of a disorder; and/or its attendant symptoms, barring a subject from acquiring a disorder or reducing a subject's risk of acquiring a disorder.

The term "therapeutically effective amount" refers to the amount of a compound that, when administered, is sufficient to prevent development of, or alleviate to some extent, one or more of the symptoms of the disorder being treated. The term "therapeutically effective amount" also refers to the amount of a compound that is sufficient to elicit the biological or medical response of a cell, tissue, system, animal, or human that is being sought by a researcher, veterinarian, medical doctor, or clinician.

The term "subject" refers to an animal, including, but not limited to, a primate (e.g., human, monkey, chimpanzee, gorilla, and the like), rodents (e.g., rats, mice, gerbils, hamsters, ferrets, and the like), lagomorphs, swine (e.g., pig, miniature pig), equine, canine, feline, and the like. The terms "subject" and "patient" are used interchangeably herein in reference, for example, to a mammalian subject, such as a human patient.

The term "combination therapy" means the administration of two or more therapeutic agents to treat a therapeutic disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the disorders described herein.

The term "chronic hyperkinetic movement disorders" refers to disorders characterized by non-purposeful, repetitive, disordered motor acts, variously termed "compulsive", "rhythmical", or "stereotyped." In humans, chronic hyperkinetic movement disorders can be psychogenic (e.g., tics), idiopathic (as in, e.g., Tourette's syndrome and Parkinson's Disease, genetic (as in, e.g., the chorea characteristic of Huntington's Disease), infectious (as in, e.g., Sydenham's Chorea), or, as in tardive dyskinesia, drug-induced. Unless otherwise stated, "chronic hyperkinetic movement disorders" refers to and includes all psychogenic, idiopathic, genetic, and drug-induced movement disorders.

The term "stereotyped" refers to a repeated behavior that appears repetitively with slight variation or, less commonly, as a complex series of movements.

The term "oppositional defiant disorder" or "ODD," refers to a psychiatric disorder characterized by aggressiveness and a tendency to purposely bother and irritate others. According to diagnostic guidelines, oppositional defiant disorder is characterized by a repeating pattern of defiant, disobedient, hostile and negative behavior toward authority figures. In one embodiment, oppositional defiant disorder occurs for at least six months. In one embodiment, oppositional defiant disorder occurs more often than other children at the same developmental level. In one embodiment, in order to be diagnosed with oppositional defiant disorder, children must exhibit four or more of the following symptoms: (1) often loses temper, (2) often argues with adults, (3) often actively defies or refuses to comply with adults' requests or rules, (4) often blames others for his or her misbehavior or mistakes, (5) is often touchy or easily annoyed by others, (6) is often angry and resentful, or (7) is often spiteful and vindictive. In one embodiment, behaviors that can be expected from a child with oppositional defiant disorder include: (1) arguing, (2) claiming not to care about losing privileges as a consequence to negative behavior, (3) continually placing blame on others, (4) not accepting responsibility for actions, (5) ignoring directives, (6) playing adults against each other (e.g. parent and teacher), (7) refusing to go to "time out," (8) resistance to directions, (9) stubbornness, (10) testing limits, and (11) unwillingness to compromise, give in, or negotiate with adults or peers.

The term "Parkinson's disease levodopa-induced dyskinesia," "levodopa-induced dyskinesia," or "LID" refers to an abnormal muscular activity disorder characterized by either disordered or excessive movement (referred to as "hyperkinesia" or "dyskinesia"), or slowness, or a lack of movement (referred to as "hypokinesia," "bradykinesia," or "akinesia"). Based on their relationship with levodopa dosing, levodopa-induced dyskinesias are classified as peak-dose, diphasic, off state, on state, and yo yo dyskinesias. Peak-dose dyskinesias are the most common forms of LID and are related to peak plasma (and possibly high striatal) levels of levodopa. They involve the head, trunk, and limbs, and sometimes respiratory muscles. Dose reduction can ameliorate them, frequently at the cost of deterioration of parkinsonism. Peak-dose dyskinesias are usually choreiform, though in the later stages dystonia can superimpose. Diphasic dyskinesias develop when plasma levodopa levels are rising or falling, but not with the peak levels. They are also called D-I-D (dyskinesia-improvement-dyskinesia). D-I-D are commonly dystonic in nature, though chorea or mixed pattern may occur. They do not respond to levodopa dose reduction and may rather improve with high dose of levodopa. "Off" state dystonias occur when plasma levodopa levels are low (for example, in the morning). They are usually pure dystonia occurring as painful spasms in one foot. They respond to levodopa therapy. Rare forms of LID include "on" state dystonias (occurring during higher levels of levodopa) and yo-yo dyskinesia (completely unpredictable pattern).

The term "VMAT2" refers to vesicular monoamine transporter 2, an integral membrane protein that acts to transport monoamines—particularly neurotransmitters such as dopamine, norepinephrine, serotonin, and histamine—from cellular cytosol into synaptic vesicles.

The term "VMAT2-mediated disorder," refers to a disorder that is characterized by abnormal VMAT2 activity. A VMAT2-mediated disorder may be completely or partially mediated by modulating VMAT2. In particular, a VMAT2-mediated disorder is one in which inhibition of VMAT2 results in some effect on the underlying disorder e.g., administration of a VMAT2 inhibitor results in some improvement in at least some of the patients being treated.

The term "VMAT2 inhibitor", "inhibit VMAT2", or "inhibition of VMAT2" refers to the ability of a compound disclosed herein to alter the function of VMAT2. A VMAT2 inhibitor may block or reduce the activity of VMAT2 by forming a reversible or irreversible covalent bond between the inhibitor and VMAT2 or through formation of a noncovalently bound complex. Such inhibition may be manifest only in particular cell types or may be contingent on a particular biological event. The term "VMAT2 inhibitor", "inhibit VMAT2", or "inhibition of VMAT2" also refers to altering the function of VMAT2 by decreasing the probability that a complex forms between a VMAT2 and a natural substrate.

The term "deuterated analog of" refers to a compound having an identical chemical structure as a given non-isotopically enriched, wherein one or more hydrogen-containing positions on the non-isotopically enriched molecule are enriched with deuterium above the naturally occurring level.

The term "deuterated analog of pirfenidone" can be defined by reference to the general structural formulas and specific compounds of U.S. Pat. No. 8,383,823, which is hereby incorporated by reference in its entirety.

The term "deuterated analog of phenylephrine" can be defined by reference to the general structural formulas and specific compounds of U.S. Pat. No. 7,745,665, which is hereby incorporated by reference in its entirety.

The term "deuterated analog of ethambutol" can be defined by reference to the general structural formulas and specific compounds of U.S. Pat. No. 7,767,860, which is hereby incorporated by reference in its entirety.

The term "deuterated analog of venlafaxine" can be defined by reference to the general structural formulas and specific compounds of U.S. Pat. No. 7,456,317, which is hereby incorporated by reference in its entirety.

The term "deuterated analog of zolipidem" can be defined by reference to the general structural formulas and specific compounds of U.S. Pat. No. 7,772,248, which is hereby incorporated by reference in its entirety.

The terms "deuterated analog of esomeprazole, lansoprazole, omeprazole, pantoprazole, or rabeprazole" can be defined by reference to the general structural formulas and specific compounds of U.S. Pat. No. 7,598,273, which is hereby incorporated by reference in its entirety.

The term "deuterated analog of sitaxentan" can be defined by reference to the general structural formulas and specific compounds of U.S. Pat. No. 7,863,308, which is hereby incorporated by reference in its entirety.

The term "deuterated analog of codeine, hydrocodone, morphine, or oxycodone" can be defined by reference to the general structural formulas and specific compounds of U.S. Pat. No. 7,872,013, which is hereby incorporated by reference in its entirety.

The term "deuterated analog of almotriptan, eletriptan, naratriptan, sumatriptan, or zolmitriptan" can be defined by reference to the general structural formulas and specific compounds of U.S. Patent Publication No. 20080103189, which is hereby incorporated by reference in its entirety.

The term "deuterated analog of ketamine" can be defined by reference to the general structural formulas and specific compounds of U.S. Pat. No. 7,638,651, which is hereby incorporated by reference in its entirety.

The term "deuterated analog of ranolazine" can be defined by reference to the general structural formulas and specific compounds of U.S. Patent Publication No. 20080312247, which is hereby incorporated by reference in its entirety.

The term "deuterated analog of desmethylvenlafaxine" can be defined by reference to the general structural formulas and specific compounds of U.S. Patent Publication No. 20080234257, which is hereby incorporated by reference in its entirety.

The term "deuterated analog of mirabegron" can be defined by reference to the general structural formulas and specific compounds of U.S. Pat. No. 8,586,760, which is hereby incorporated by reference in its entirety.

The term "deuterated analog of ticagrelor" can be defined by reference to the general structural formulas and specific compounds of U.S. Patent Publication No. 20120301458, which is hereby incorporated by reference in its entirety.

The term "deuterated analog of darapladib" can be defined by reference to the general structural formulas and specific compounds of U.S. Patent Publication No. 20110306552, which is hereby incorporated by reference in its entirety.

The term "deuterated analog of rilapladib" can be defined by reference to the general structural formulas and specific compounds of U.S. Pat. No. 8,575,348, which is hereby incorporated by reference in its entirety.

The term "deuterated analog of nilotinib" can be defined by reference to the general structural formulas and specific compounds of U.S. Patent Publication No. 20110053968, which is hereby incorporated by reference in its entirety.

The term "deuterated analog of tofacitinib" can be defined by reference to the general structural formulas and specific compounds of U.S. Pat. No. 8,299,084, which is hereby incorporated by reference in its entirety.

The term "deuterated analog of apixaban" can be defined by reference to the general structural formulas and specific compounds of U.S. Patent Publication No. 20100130543, which is hereby incorporated by reference in its entirety.

The term "deuterated analog of lumiracoxib" can be defined by reference to the general structural formulas and specific compounds of U.S. Pat. No. 8,227,451, which is hereby incorporated by reference in its entirety.

The term "deuterated analog of solabegron" can be defined by reference to the general structural formulas and specific compounds of U.S. Patent Publication No. 20100120861, which is hereby incorporated by reference in its entirety.

The term "deuterated analog of riociguat" can be defined by reference to the general structural formulas and specific compounds of U.S. Patent Publication No. 20110201626, which is hereby incorporated by reference in its entirety.

The term "deuterated analog of cariprazine" can be defined by reference to the general structural formulas and specific compounds of U.S. Patent Publication No. 20110117214, which is hereby incorporated by reference in its entirety.

The term "deuterated analog of neratinib or pelitinib" can be defined by reference to the general structural formulas and specific compounds of PCT Publication No. WO 2011123524, which is hereby incorporated by reference in its entirety.

The term "deuterated analog of fostamatinib or R-406" can be defined by reference to the general structural formulas and specific compounds of U.S. Patent Publication No. 20110206661, which is hereby incorporated by reference in its entirety.

The term "deuterated analog of dihydrotetrabenazine" can be defined by reference to the general structural formulas and specific compounds of U.S. Patent Publication No. 20120003330, which is hereby incorporated by reference in its entirety.

The term "deuterated analog of L-838417" can be defined by reference to the general structural formulas and specific compounds of PCT Publication Nos. WO2010025407, WO2013170242, and WO2013170243, each of which are hereby incorporated by reference in its entirety.

The term "deuterated analog of pentoxifylline or pentoxifylline metabolites" can be defined by reference to the general structural formulas and specific compounds of PCT Publication Nos. WO 2009108375, WO 2009108383, WO 2012031073, WO 2012031072, and WO 2013159006, each of which are hereby incorporated by reference in their entireties.

The term "deuterated analog of levodopa" can be defined by reference to the general structural formulas and specific compounds of PCT Publication No. WO 2007093450, which is hereby incorporated by reference in its entirety.

The term "deuterated analog of carbidopa" refers to an analog of carbidopa wherein one or more hydrogen-containing positions on the non-isotopically enriched molecule are enriched with deuterium above the naturally occurring level.

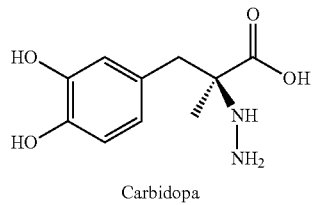 [SMILES: C[C@@](Cc1ccc(O)c(O)c1)(NN)C(=O)O]

Carbidopa

Non-isotopically enriched carbidopa is described in Falck, Drug Intel. Clin. Pharm., 1976, 10(2), 84-5; Pinder et al., Drugs, 1976, 11(5), 329-77; and Rao et al., Adv. Neurol., 1973, 3, 73-7; each of which are hereby incorporated by reference in their entireties.

The term "deuterated analog of amantidine" refers to an analog of amantidine wherein one or more hydrogen-containing positions on the non-isotopically enriched molecule are enriched with deuterium above the naturally occurring level.

Amantidine

Non-isotopically enriched amantidine is described in Danielczyk, J. Neural. Trans., Suppl., 1995, 46 (Parkinsons Disease: Experimental Models and Therapy), 399-405; Ebadi et al., Parkinson's Disease, 2005, 685-690; Singer et al., J. Appl. Res. (2006), 6(3), 240-245; Dashtipour et al., Neurol. Disease Ther., 2007, 92 (Handbook of Parkinson's Disease (4th Edition)), 293-307, each of which are hereby incorporated by reference in their entireties.

The term "deuterated analog of nintedanib" refers to an analog of nintedanib wherein one or more hydrogen-containing positions on the non-isotopically enriched molecule are enriched with deuterium above the naturally occurring level.

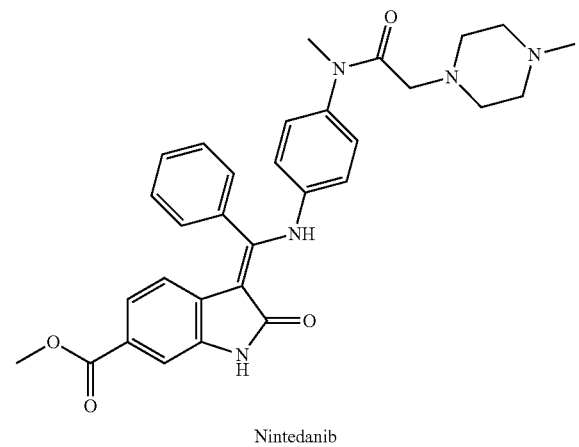

Nintedanib

Non-isotopically enriched nintedanib is described in Roth et al., J. Med. Chem., 2009, 52(14), 4466-4480; WO 2004017948; WO 2006067165; and U.S. Pat. No. 6,762,180, each of which are hereby incorporated by reference in their entireties.

The term "deuterated analog of pridopidine" can be defined by reference to the general structural formulas and specific compounds of PCT Publication No. WO 2012028635, which is hereby incorporated by reference in its entirety.

The term "deuterated analog of dipraglurant" refers to an analog of dipraglurant wherein one or more hydrogen-containing positions on the non-isotopically enriched molecule are enriched with deuterium above the naturally occurring level.

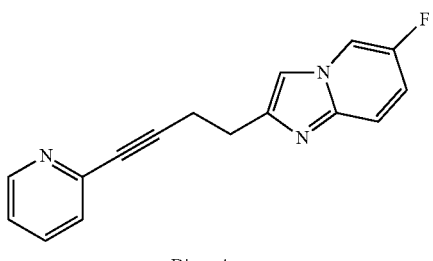

Dipraglurant

Non-isotopically enriched dipraglurant is described as compound of Example 74 of PCT Publication Nos. WO 2005123703, and further described in WO 2013186311, each of which are hereby incorporated by reference in their entireties.

The term "therapeutically acceptable" refers to those compounds (or salts, prodrugs, tautomers, zwitterionic forms, etc.) which are suitable for use in contact with the tissues of patients without excessive toxicity, irritation, allergic response, immunogenecity, are commensurate with a reasonable benefit/risk ratio, and are effective for their intended use.

The term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, excipient, solvent, or encapsulating material. Each component must be "pharmaceutically acceptable" in the sense of being compatible with the other ingredients of a pharmaceutical formulation. It must also be suitable for use in contact with the tissue or organ of humans and animals without excessive toxicity, irritation, allergic response, immunogenecity, or other problems or complications, commensurate with a reasonable benefit/risk ratio. See, *Remington: The Science and Practice of Pharmacy*, 21st Edition; Lippincott Williams & Wilkins: Philadelphia, Pa., 2005; *Handbook of Pharmaceutical Excipients*, 5th Edition; Rowe et al., Eds., The Pharmaceutical Press and the American Pharmaceutical Association: 2005; and *Handbook of Pharmaceutical Additives*, 3rd Edition; Ash and Ash Eds., Gower Publishing Company: 2007; *Pharmaceutical Preformulation and Formulation*, Gibson Ed., CRC Press LLC: Boca Raton, Fla., 2004).

The terms "active ingredient," "active compound," and "active substance" refer to a compound, which is administered, alone or in combination with one or more pharmaceutically acceptable excipients or carriers, to a subject for treating, preventing, or ameliorating one or more symptoms of a disorder.

The terms "drug," "therapeutic agent," and "chemotherapeutic agent" refer to a compound, or a pharmaceutical composition thereof, which is administered to a subject for treating, preventing, or ameliorating one or more symptoms of a disorder.

The terms "extended release," "extended release formulation," "sustained release," and "sustained release formulation," refers to a dosage form containing a release controlling excipient, wherein the duration or place of release of the active substance from a dosage form is delayed when compared with a conventional immediate release dosage form. In certain embodiments an extended release dosage form results in an active substance plasma concentration that is characterized by a slower rate of rise (delayed $T_{max}$) or a lower peak concentration (lower dose-normalized $C_{max}$). In certain embodiments an extended release dosage form results in similar or greater systemic exposure (AUC) as a conventional immediate release dosage form having an equivalent amount of active substance.

The term "release controlling excipient" refers to an excipient whose primary function is to modify the duration or place of release of the active substance from a dosage form as compared with a conventional immediate release dosage form.

The term "nonrelease controlling excipient" refers to an excipient whose primary function do not include modifying the duration or place of release of the active substance from a dosage form as compared with a conventional immediate release dosage form.

The term "prodrug" refers to a compound functional derivative of the compound as disclosed herein and is readily convertible into the parent compound in vivo. Prodrugs are often useful because, in some situations, they may be easier to administer than the parent compound. They may, for instance, be bioavailable by oral administration whereas the parent compound is not. The prodrug may also have enhanced solubility in pharmaceutical compositions over the parent compound. A prodrug may be converted into the parent drug by various mechanisms, including enzymatic processes and metabolic hydrolysis. See Harper, Progress in Drug Research 1962, 4, 221-294; Morozowich et al. in "Design of Biopharmaceutical Properties through Prodrugs and Analogs," Roche Ed., APHA Acad. Pharm. Sci. 1977; "Bioreversible Carriers in Drug in Drug Design, Theory and Application," Roche Ed., APHA Acad. Pharm. Sci. 1987; "Design of Prodrugs," Bundgaard, Elsevier, 1985; Wang et al., Curr. Pharm. Design 1999, 5, 265-287; Pauletti et al., Adv. Drug. Delivery Rev. 1997, 27, 235-256; Mizen et al., Pharm. Biotech. 1998, 11, 345-365; Wermuth et al., Pract. Med. Chem. 1996, 671-696; Asghamejad in "Transport Processes in Pharmaceutical Systems," Amidon et al., Ed., Marcell Dekker, 185-218, 2000; Balant et al., Eur. J. Drug Metab. Pharmacokinet. 1990, 15, 143-53; Balimane and Sinko, Adv. Drug Delivery Rev. 1999, 39, 183-209; Browne, Clin. Neuropharmacol. 1997, 20, 1-12; Bundgaard, Arch. Pharm. Chem. 1979, 86, 1-39; Heller J., Controlled Drug Delivery 1987, 17, 179-96; Bundgaard, Adv. Drug Delivery Rev. 1992, 8, 1-38; Fleisher et al., Adv. Drug Delivery Rev. 1996, 19, 115-130; Fleisher et al., Methods Enzymol. 1985, 112, 360-381; Farquhar et al., J. Pharm. Sci. 1983, 72, 324-325; Freeman et al., J. Chem. Soc., Chem. Commun. 1991, 875-877; Friis and Bundgaard, Eur. J. Pharm. Sci. 1996, 4, 49-59; Gangwar et al., Des. Biopharm. Prop. Prodrugs Analogs, 1977, 409-421; Nathwani and Wood, Drugs 1993, 45, 866-94; Sinhababu and Thakker, Adv. Drug Delivery Rev. 1996, 19, 241-273; Stella et al., Drugs 1985, 29, 455-73; Tan et al., Adv. Drug Delivery Rev. 1999, 39, 117-151; Taylor, Adv. Drug Delivery Rev. 1996, 19, 131-148; Gangwar, Drug Discovery Today 1997, 2, 148-155; Wiebe and Knaus, Adv. Drug Delivery Rev. 1999, 39, 63-80; Waller et al., Br. J. Clin. Pharmac. 1989, 28, 497-507.

The compounds disclosed herein can exist as therapeutically acceptable salts. The term "therapeutically acceptable salt," as used herein, represents salts or zwitterionic forms of the compounds disclosed herein which are therapeutically acceptable as defined herein. The salts can be prepared during the final isolation and purification of the compounds or separately by reacting the appropriate compound with a suitable acid or base. Therapeutically acceptable salts include acid and basic addition salts. For a more complete discussion of the preparation and selection of salts, refer to "Handbook of Pharmaceutical Salts, Properties, and Use," Stah and Wermuth, Ed., (Wiley-VCH and VHCA, Zurich, 2002) and Berge et al., *J. Pharm. Sci.* 1977, 66, 1-19.

Suitable acids for use in the preparation of pharmaceutically acceptable salts include, but are not limited to, acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxo-glutaric acid, glycolic acid, hippuric acid, hydrobromic acid, hydrochloric acid, hydroiodic acid, (+)-L-lactic acid, (±)-DL-lactic acid, lactobionic acid, lauric acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

Suitable bases for use in the preparation of pharmaceutically acceptable salts, including, but not limited to, inorganic bases, such as magnesium hydroxide, calcium hydroxide, potassium hydroxide, zinc hydroxide, or sodium hydroxide; and organic bases, such as primary, secondary, tertiary, and quaternary, aliphatic and aromatic amines, including L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methylglucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glucamine, 2-amino-2-(hydroxymethyl)-1,3-propanediol, and tromethamine.

References to a compound of a formula and subgroups thereof include ionic forms, polymorphs, pseudopolymorphs, amorphous forms, and solvates thereof "Crystalline form," "polymorph," and "novel form" may be used interchangeably herein, and are meant to include all crystalline and amorphous forms of the compound, including, for example, polymorphs, pseudopolymorphs, solvates (including hydrates), co crystals, unsolvated polymorphs (including anhydrates), conformational polymorphs, and amorphous forms, as well as mixtures thereof, unless a particular crystalline or amorphous form is referred to. In some embodiments, references to a compound include polymorphs, solvates, and/or co crystals thereof. In some embodiments, references to a compound of a formula and subgroups thereof include polymorphs thereof. Similarly, the term "salts" includes polymorphs of salts of compounds.

Pharmaceutical Formulations

While it may be possible for the compounds of the subject invention to be administered as the raw chemical, it is also possible to present them as a pharmaceutical composition. Accordingly, provided herein are pharmaceutical compositions which comprise one or more of certain compounds disclosed herein, or one or more pharmaceutically acceptable salts, prodrugs, or solvates thereof, together with one or more pharmaceutically acceptable carriers thereof and optionally one or more other therapeutic ingredients. Proper formulation is dependent upon the route of administration chosen. Any of the well-known techniques, carriers, and excipients may be used as suitable and as understood in the art; e.g., in Remington's Pharmaceutical Sciences. The pharmaceutical compositions disclosed herein may be manufactured in any manner known in the art, e.g., by means of conventional mixing, dissolving, granulating, dragee-making, levigating, emulsifying, encapsulating, entrapping or compression processes. The pharmaceutical compositions may also be formulated as a modified release dosage form, including delayed-, extended-, prolonged-, sustained-, pulsatile-, controlled-, accelerated- and fast-, targeted-, programmed-release, and gastric retention dosage forms. These dosage forms can be prepared according to conventional methods and techniques known to those skilled in the art (see, *Remington: The Science and Practice of Pharmacy*, supra; *Modified-Release Drug Deliver Technology*, Rathbone et al., Eds., Drugs and the Pharmaceutical Science, Marcel Dekker, Inc., New York, N.Y., 2002; Vol. 126).

The compositions include those suitable for oral administration. The compositions may conveniently be presented in unit dosage form and may be prepared by any of the methods well known in the art of pharmacy. Typically, these methods include the step of bringing into association a compound of the subject invention or a pharmaceutically salt, prodrug, or solvate thereof ("active ingredient") with the carrier which constitutes one or more accessory ingredients. In general, the compositions are prepared by uniformly and intimately bringing into association the active ingredient with liquid carriers or finely divided solid carriers or both and then, if necessary, shaping the product into the desired formulation.

Formulations of the compounds disclosed herein suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

In certain embodiments, diluents are selected from the group consisting of mannitol powder, spray dried mannitol, microcrystalline cellulose, lactose, dicalcium phosphate, tricalcium phosphate, starch, pregelatinized starch, compressible sugars, silicified microcrystalline cellulose, and calcium carbonate.

In certain embodiments, surfactants are selected from the group consisting of Tween 80, sodium lauryl sulfate, and docusate sodium.

In certain embodiments, binders are selected from the group consisting of povidone (PVP) K29/32, hydroxypropylcellulose (HPC), hydroxypropylmethylcellulose (HPMC), ethylcellulose (EC), corn starch, pregelatinized starch, gelatin, and sugar.

In certain embodiments, lubricants are selected from the group consisting of magnesium stearate, stearic acid, sodium stearyl fumarate, calcium stearate, hydrogenated vegetable oil, mineral oil, polyethylene glycol, polyethylene glycol 4000-6000, talc, and glyceryl behenate.

In certain embodiments, sustained release polymers are selected from the group consisting of POLYOX® (poly (ethylene oxide), POLYOX® N60K grade, Kollidon® SR, HPMC, HPMC (high viscosity), HPC, HPC (high viscosity), and Carbopol®.

In certain embodiments, extended/controlled release coating are selected from a group of ethylcellulose polymers, such as ETHOCEL™ and Surelease® Aqueous Ethylcellulose Dispersions.

In certain embodiments, antioxidants are selected from a group consisting of butylated hydroxyanisole (BHA), butylated hydroxytoluene (BHT), sodium ascorbate, and α-tocopherol.

In certain embodiments, tablet coatings are selected from the group of Opadry® 200, Opadry® II, Opadry® fx, Opadry® amb, Opaglos® 2, Opadry® tm, Opadry®, Opadry® NS, Opalux®, Opatint®, Opaspray®, Nutraficient®.

Preferred unit dosage formulations are those containing an effective dose, as herein below recited, or an appropriate fraction thereof, of the active ingredient.

Compounds may be administered orally at a dose of from 0.1 to 500 mg/kg per day. The dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the disorder being treated. Also, the route of administration may vary depending on the disorder and its severity.

In the case wherein the patient's condition does not improve, upon the doctor's discretion the administration of the compounds may be administered chronically, that is, for an extended period of time, including throughout the duration of the patient's life in order to ameliorate or otherwise control or limit the symptoms of the patient's disorder.

In the case wherein the patient's status does improve, upon the doctor's discretion the administration of the compounds may be given continuously or temporarily suspended for a certain length of time (i.e., a "drug holiday").

Once improvement of the patient's conditions has occurred, a maintenance dose is administered if necessary. Subsequently, the dosage or the frequency of administration, or both, can be reduced, as a function of the symptoms, to a level at which the improved disorder is retained. Patients can, however, require intermittent treatment on a long-term basis upon any recurrence of symptoms.

Indications

Disclosed herein are methods of treating a VMAT2-mediated disorder comprising administering to a subject having or suspected of having such a disorder, a therapeutically effective amount of a compound or composition as disclosed herein or a pharmaceutically acceptable salt, solvate, or prodrug thereof.

VMAT2-mediated disorders, include, but are not limited to, chronic hyperkinetic movement disorders, Huntington's disease, hemiballismus, chorea associated with Huntington's disease, senile chorea, tic disorders, tardive dyskinesia, dystonia, Tourette's syndrome, depression, cancer, rheumatoid arthritis, psychosis, multiple sclerosis, asthma, Parkinson's disease levodopa-induced dyskinesia, movement disorders, and oppositional defiant disorder, and/or any disorder which can lessened, alleviated, or prevented by administering a VMAT2 inhibitor.

Movement disorders include, but are not limited to, ataxia, corticobasal degeneration, dyskinesias (paroxysmal), dystonia (general, segmental, focal) including blepharospasm, spasmodic torticollis (cervical dystonia), writer's cramp (limb dystonia), laryngeal dystonia (spasmodic dysphonia), and oromandibular dystonia, essential tremor, hereditary spastic paraplegia, Huntington's Disease, multiple system atrophy (Shy Drager Syndrome), myoclonus, Parkinson's Disease, progressive supranuclear palsy, restless legs syndrome, Rett Syndrome, spasticity due to stroke, cerebral palsy, multiple sclerosis, spinal cord or brain injury, Sydenham's Chorea, tardive dyskinesia/dystonia, tics, Tourette's Syndrome, and Wilson's Disease.

Plasma levels of the compound as disclosed herein, or metabolites thereof, may be measured using the methods described by Li et al. *Rapid Communications in Mass Spectrometry* 2005, 19, 1943-1950; Jindal, et al., *Journal of Chromatography, Biomedical Applications* 1989, 493(2), 392-7; Schwartz, et al., *Biochemical Pharmacology* 1966, 15(5), 645-55; Mehvar, et al., *Drug Metabolism and Disposition* 1987, 15(2), 250-5; Roberts et al., *Journal of Chromatography, Biomedical Applications* 1981, 226(1), 175-82; and any references cited therein or any modifications made thereof.

Examples of cytochrome $P_{450}$ isoforms in a mammalian subject include, but are not limited to, CYP1A1, CYP1A2, CYP1B1, CYP2A6, CYP2A13, CYP2B6, CYP2C8, CYP2C9, CYP2C18, CYP2C19, CYP2D6, CYP2E1, CYP2G1, CYP2J2, CYP2R1, CYP2S1, CYP3A4, CYP3A5, CYP3A5P1, CYP3A5P2, CYP3A7, CYP4A11, CYP4B1, CYP4F2, CYP4F3, CYP4F8, CYP4F11, CYP4F12, CYP4X1, CYP4Z1, CYP5A1, CYP7A1, CYP7B1, CYP8A1, CYP8B1, CYP11A1, CYP11B1, CYP11B2, CYP17, CYP19, CYP21, CYP24, CYP26A1, CYP26B1, CYP27A1, CYP27B1, CYP39, CYP46, and CYP51.

Examples of monoamine oxidase isoforms in a mammalian subject include, but are not limited to, $MAO_A$, and $MAO_B$.

The inhibition of the cytochrome $P_{450}$ isoform is measured by the method of Ko et al. (*British Journal of Clinical Pharmacology*, 2000, 49, 343-351). The inhibition of the $MAO_A$ isoform is measured by the method of Weyler et al. (*J. Biol Chem.* 1985, 260, 13199-13207). The inhibition of the $MAO_B$ isoform is measured by the method of Uebelhack et al. (*Pharmacopsychiatry*, 1998, 31, 187-192).

Examples of polymorphically-expressed cytochrome $P_{450}$ isoforms in a mammalian subject include, but are not limited to, CYP2C8, CYP2C9, CYP2C19, and CYP2D6.

The metabolic activities of liver microsomes, cytochrome $P_{450}$ isoforms, and monoamine oxidase isoforms are measured by the methods described herein.

Examples of improved disorder-control and/or disorder-eradication endpoints, or improved clinical effects include, but are not limited to, change from baseline in the chorea score of the Unified Huntington's Disease Rating Scale (UHDRS).

Examples of improved disorder-control and/or disorder-eradication endpoints, or improved clinical effects include, but are not limited to:

a. improved Unified Parkinson's Disease Rating Scale scores;
b. improved Abnormal Involuntary Movement Scale scores;
c. improved Goetz Dyskinesia Rating Scale scores;
d. improved Unified Dyskinesia Rating Scale scores;
e. improved PDQ-39 Parkinson's Disease Questionnaire scores; and
f. improved Global Primate Dyskinesia Rating Scale scores.

Examples of improved disorder-control and/or disorder-eradication endpoints, or improved clinical effects in the treatment of oppositional defiant disorder include, but are not limited to:

a. reduced aggressiveness;
b. reduction of the rate or severity of incidents of temper loss;
c. reduction of the rate or severity of incidents of arguing with adults;
d. reduction of the rate or severity of incidents of defiance or refusal to comply with adults' requests or rules;
e. reduction of the rate or severity of incidents of blaming others for his or her misbehavior or mistakes;
f. reduced touchiness or ease of annoyance by others;
g. reduced anger and/or resentfulness;
h. reduced spitefulness and/or vindictiveness;
i. reduction of the rate or severity of incidents of arguing;
j. reduction of the rate or severity of incidents of claiming not to care about losing privileges as a consequence to negative behavior;
k. reduction of the rate or severity of incidents of placing blame on others;
l. reduction of the rate or severity of incidents of not accepting responsibility for actions;
m. reduction of the rate or severity of incidents of ignoring directives;
n. reduction of the rate or severity of incidents of playing adults against each other;
o. reduction of the rate or severity of incidents of refusing to go to "time out";
p. reduction of the rate or severity of incidents of resisting directions;
q. reduced stubbornness;
r. reduction of the rate or severity of incidents of testing limits; and
s. reduction of the rate or severity of incidents of unwillingness to compromise, give in, or negotiate with adults or peers.

Examples of diagnostic hepatobiliary function endpoints include, but are not limited to, alanine aminotransferase ("ALT"), serum glutamic-pyruvic transaminase ("SGPT"), aspartate aminotransferase ("AST" or "SGOT"), ALT/AST ratios, serum aldolase, alkaline phosphatase ("ALP"), ammonia levels, bilirubin, gamma-glutamyl transpeptidase ("GGTP," "γ-GTP," or "GGT"), leucine aminopeptidase ("LAP"), liver biopsy, liver ultrasonography, liver nuclear scan, 5'-nucleotidase, and blood protein. Hepatobiliary endpoints are compared to the stated normal levels as given in "Diagnostic and Laboratory Test Reference", $4^{th}$ edition, Mosby, 1999. These assays are run by accredited laboratories according to standard protocol.

Besides being useful for human treatment, certain compounds and formulations disclosed herein may also be useful for veterinary treatment of companion animals, exotic animals and farm animals, including mammals, rodents, and the like. More preferred animals include horses, dogs, and cats.

Combination Therapy

The compounds disclosed herein may also be combined or used in combination with other agents useful in the treatment of VMAT2-mediated disorders. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced).

Such other agents, adjuvants, or drugs, may be administered, by a route and in an amount commonly used therefor, simultaneously or sequentially with a compound as disclosed herein. When a compound as disclosed herein is used contemporaneously with one or more other drugs, a pharmaceutical composition containing such other drugs in addition to the compound disclosed herein may be utilized, but is not required.

In certain embodiments, the compounds disclosed herein can be combined with one or more dopamine precursors, including, but not limited to, levodopa.

In certain embodiments, the compounds disclosed herein can be combined with one or more DOPA decarboxylase inhibitors, including, but not limited to, carbidopa.

In certain embodiments, the compounds disclosed herein can be combined with one or more catechol-O-methyl transferase (COMT) inhibitors, including, but not limited to, entacapone and tolcapone.

In certain embodiments, the compounds disclosed herein can be combined with one or more dopamine receptor agonists, including, but not limited to, apomorphine, bromocriptine, ropinirole, and pramipexole.

In certain embodiments, the compounds disclosed herein can be combined with one or more neuroprotective agents, including, but not limited to, selegeline and riluzole.

In certain embodiments, the compounds disclosed herein can be combined with one or more NMDA antagonists, including, but not limited to, amantidine.

In certain embodiments, the compounds disclosed herein can be combined with one or more anti-psychotics, including, but not limited to, chlorpromazine, levomepromazine, promazine, acepromazine, triflupromazine, cyamemazine, chlorproethazine, dixyrazine, fluphenazine, perphenazine, prochlorperazine, thiopropazate, trifluoperazine, acetophenazine, thioproperazine, butaperazine, perazine, periciazine, thioridazine, mesoridazine, pipotiazine, haloperidol, trifluperidol, melperone, moperone, pipamperone, bromperidol, benperidol, droperidol, fluanisone, oxypertine, molindone, sertindole, ziprasidone, flupentixol, clopenthixol, chlorprothixene, thiothixene, zuclopenthixol, fluspirilene, pimozide, penfluridol, loxapine, clozapine, olanzapine, quetiapine, tetrabenazine, sulpiride, sultopride, tiapride, remoxipride, amisulpride, veralipride, levosulpiride, lithium, prothipendyl, risperidone, clotiapine, mosapramine, zotepine, pripiprazole, and paliperidone.

In certain embodiments, the compounds disclosed herein can be combined with one or more benzodiazepines ("minor tranquilizers"), including, but not limited to alprazolam, adinazolam, bromazepam, camazepam, clobazam, clonazepam, clotiazepam, cloxazolam, diazepam, ethyl loflazepate, estizolam, fludiazepam, flunitrazepam, halazepam, ketazolam, lorazepam, medazepam, dazolam, nitrazepam, nordazepam, oxazepam, potassium clorazepate, pinazepam, prazepam, tofisopam, triazolam, temazepam, and chlordiazepoxide.

In certain embodiments, the compounds disclosed herein can be combined with olanzapine or pimozide.

The compounds disclosed herein can also be administered in combination with other classes of compounds, including, but not limited to, anti-retroviral agents; CYP3A inhibitors; CYP3A inducers; protease inhibitors; adrenergic agonists; anti-cholinergics; mast cell stabilizers; xanthines; leukotriene antagonists; glucocorticoids treatments; local or general anesthetics; non-steroidal anti-inflammatory agents (NSAIDs), such as naproxen; antibacterial agents, such as amoxicillin; cholesteryl ester transfer protein (CETP) inhibitors, such as anacetrapib; anti-fungal agents, such as isoconazole; sepsis treatments, such as drotrecogin-α; steroidals, such as hydrocortisone; local or general anesthetics, such as ketamine; norepinephrine reuptake inhibitors (NRIs) such as atomoxetine; dopamine reuptake inhibitors (DARIs), such as methylphenidate; serotonin-norepinephrine reuptake inhibitors (SNRIs), such as milnacipran; sedatives, such as diazepham; norepinephrine-dopamine reuptake inhibitor (NDRIs), such as bupropion; serotonin-norepinephrine-dopamine-reuptake-inhibitors (SNDRIs), such as venlafaxine; monoamine oxidase inhibitors, such as selegiline; hypothalamic phospholipids; endothelin converting enzyme (ECE) inhibitors, such as phosphoramidon; opioids, such as tramadol; thromboxane receptor antagonists, such as ifetroban; potassium channel openers; thrombin inhibitors, such as hirudin; hypothalamic phospholipids; growth factor inhibitors, such as modulators of PDGF activity; platelet activating factor (PAF) antagonists; anti-platelet agents, such as GPIIb/IIIa blockers (e.g., abdximab, eptifibatide, and tirofiban), P2Y(AC) antagonists (e.g., clopidogrel, ticlopidine and CS-747), and aspirin; anticoagulants, such as warfarin; low molecular weight heparins, such as enoxaparin; Factor VIIa Inhibitors and Factor Xa Inhibitors; renin inhibitors; neutral endopeptidase (NEP) inhibitors; vasopepsidase inhibitors (dual NEP-ACE inhibitors), such as omapatrilat and gemopatrilat; HMG CoA reductase inhibitors, such as pravastatin, lovastatin, atorvastatin, simvastatin, NK-104 (a.k.a. itavastatin, nisvastatin, or nisbastatin), and ZD-4522 (also known as rosuvastatin, or atavastatin or visastatin); squalene synthetase inhibitors; fibrates; bile acid sequestrants, such as questran; niacin; anti-atherosclerotic agents, such as ACAT inhibitors; MTP Inhibitors; calcium channel blockers, such as amlodipine besylate; potassium channel activators; alpha-muscarinic agents; beta-muscarinic agents, such as carvedilol and metoprolol; antiarrhythmic agents; diuretics, such as chlorothlazide, hydrochlorothiazide, flumethiazide, hydroflumethiazide, bendroflumethiazide, methylchlorothiazide, trichioromethiazide, polythiazide, benzothlazide, ethacrynic acid, tricrynafen, chlorthalidone, furosenilde, musolimine, bumetanide, triamterene, amiloride, and spironolactone; thrombolytic agents, such as tissue plasminogen activator (tPA), recombinant tPA, streptokinase, urokinase, prourokinase, and anisoylated plasminogen streptokinase activator complex (APSAC); anti-diabetic agents, such as biguanides (e.g. metformin), glucosidase inhibitors (e.g., acarbose), insulins, meglitinides (e.g., repaglinide), sulfonylureas (e.g., glimepiride, glyburide, and glipizide), thiozolidinediones (e.g. troglitazone, rosiglitazone and pioglitazone), and PPAR-gamma agonists; mineralocorticoid receptor antagonists, such as spironolactone and eplerenone; growth hormone secretagogues; aP2 inhibitors; phosphodiesterase inhibitors, such as PDE III inhibitors (e.g., cilostazol) and PDE V inhibitors (e.g., sildenafil, tadalafil, vardenafil); protein tyrosine kinase inhibitors; antiinflammatories; antiproliferatives, such as methotrexate, FK506 (tacrolimus, Prograf), mycophenolate mofetil; chemotherapeutic agents; immunosuppressants; anticancer agents and cytotoxic agents (e.g., alkylating agents, such as nitrogen mustards, alkyl sulfonates, nitrosoureas, ethylenimines, and triazenes); antimetabolites, such as folate antagonists, purine analogues, and pyrridine analogues; antibiotics, such as anthracyclines, bleomycins, mitomycin, dactinomycin, and plicamycin; enzymes, such as L-asparaginase; farnesyl-protein transferase inhibitors; hormonal agents, such as glucocorticoids (e.g., cortisone), estrogens/antiestrogens, androgens/antiandrogens, progestins, and luteinizing hormone-releasing hormone antagonists, and octreotide acetate; microtubule-disrupter agents, such as ecteinascidins; microtubule-stabilizing agents, such as paclitaxel, docetaxel, and epothilones A-F; plant-derived products, such as vinca alkaloids, epipodophyllotoxins, and taxanes; and topoisomerase inhibitors; prenyl-protein transferase inhibitors; and cyclosporins; steroids, such as prednisone and dexamethasone; cytotoxic drugs, such as azathiprine and cyclophosphamide; TNF-alpha inhibitors, such as tenidap; anti-TNF antibodies or soluble TNF receptor, such as etanercept, rapamycin, and leflunimide; and cyclooxygenase-2 (COX-2) inhibitors, such as celecoxib and rofecoxib; and miscellaneous agents such as, hydroxyurea, procarbazine, mitotane, hexamethylmelamine, gold compounds, platinum coordination complexes, such as cisplatin, satraplatin, and carboplatin.

Thus, in another aspect, certain embodiments provide methods for treating VMAT2-mediated disorders in a subject in need of such treatment comprising administering to said subject an amount of a compound disclosed herein effective to reduce or prevent said disorder in the subject, in combination with at least one additional agent for the treatment of said disorder. In a related aspect, certain embodiments provide therapeutic compositions comprising at least one compound disclosed herein in combination with one or more additional agents for the treatment of VMAT2-mediated disorders.

General Synthetic Methods for Preparing Compounds

The compounds as disclosed herein can be prepared by methods known to one of skill in the art and routine modifications thereof, and/or following procedures similar to those described in US 20100130480 (paragraphs [0093]-[0121]), US 20120003330 (paragraphs [0104]-[0162]), WO 2005077946; WO 2008/058261; EP 1716145; Lee et al., J. Med. Chem., 1996, (39), 191-196; Kilbourn et al., Chirality, 1997, (9), 59-62; Boldt et al., Synth. Commun., 2009, (39), 3574-3585; Rishel et al., J. Org. Chem., 2009, (74), 4001-4004; DaSilva et al., Appl. Radiat. Isot., 1993, 44(4), 673-676; Popp et al., J. Pharm. Sci., 1978, 67(6), 871-873; Ivanov et al., Heterocycles 2001, 55(8), 1569-1572; U.S. Pat. No. 2,830,993; U.S. Pat. No. 3,045,021; WO 2007130365; WO 2008058261; U.S. Pat. No. 7,638,651; U.S. Pat. No. 8,383,823; U.S. Pat. No. 7,745,665; U.S. Pat. No. 7,767,860; U.S. Pat. No. 7,456,317; U.S. Pat. No. 7,772,248; U.S. Pat. No. 7,598,273; U.S. Pat. No. 7,863,308; U.S. Pat. No. 7,872,013; US 20080103189; U.S. Pat. No. 7,638,651; US 20080312247; US 20080234257; U.S. Pat. No. 8,586,760; US 20120301458; US 20110306552; U.S.

Pat. No. 8,575,348; US 20110053968; U.S. Pat. No. 8,299,084; US 20100130543; U.S. Pat. No. 8,227,451; US 20100120861; US 20110201626; US 20110117214; WO 2011123524; US 20110206661; US 20120003330; WO2010025407; WO2013170242; WO2013170243; WO 2009108375; WO 2009108383; WO 2012031073; WO 2012031072; and WO 2013159006, which are hereby incorporated in their entirety, and references cited therein and routine modifications thereof.

The invention is further illustrated by the following examples.

FORMULATION EXAMPLES

Examples 1-5, and other Examples described herein, may be made by the methods disclosed in FIG. 1.

Example 1

25 mg Tetrabenazine Gastro-Erosional Extended Release (Small Tablet) (Formulation A)

Table 1 below discloses the elements of a 350 mg total weight gastro-erosional granulation formulation tablet comprising 25 mg (RR, SS)-1,3,4,6,7,11b-hexahydro-9,10-di(methoxy)-3-(2-methylpropyl)-2H-benzo[a]quinolizin-2-one.

TABLE 1

| Material | mg/tab | % |
|---|---|---|
| Tetrabenazine (milled) | 25 | 7.1 |
| Mannitol Powder | 177.9 | 50.8 |
| Microcrystalline Cellulose | 59.3 | 16.9 |
| PVP K29/32 | 14 | 4.0 |
| Tween 80 (Polysorbate 80) | 3.8 | 1.1 |
| Mannogem ® EZ (spray dried mannitol) | 31.5 | 9.0 |
| POLYOX ® N60K | 35 | 10.0 |
| Magnesium Stearate | 3.5 | 1.0 |
| Totals: | 350.0 | 100.0 |

Tetrabenazine (milled) is combined along with Mannitol Powder, Microcrystalline Cellulose, PVP K29/32 and Tween 80 (Polysorbate 80) into a high shear granulator and initially dry mixed at high impeller and chopper speed for 5 minutes. While mixing at high impeller speed and low chopper speed, Purified Water is added to the mixing powders to granulate the material. Additional mixing and water addition with high impeller and high chopper speed continues until the desired granulation end-point is achieved. The resulting granulation is wet screened to break up any oversized agglomerates and the material is added to a fluid bed drier and dried at 60° C. until the desired L.O.D. (loss on drying) is achieved. The dried material is sieved through a #20 mesh screen and the oversized material is milled to a particle size of just under 20 mesh in size. The dried and sized material is combined with Spray Dried Mannitol and POLYOX® N60K into a diffusive mixer (V-Blender) where it is blended for 15 minutes. Magnesium Stearate is then passed through a #30 mesh screen and added to the blended material in the V-Blender. The contents are then lubricated for 3 minutes and discharged for tablet compression. Using a rotary tablet press fitted with punches and dies of the desired shape and size, the lubricated blend is compressed into tablets of a theoretical weight of 350 mg.

Example 2

15 mg Tetrabenazine Gastro-Erosional Extended Release (Small Tablet) (Formulation A)

Table 2 below discloses the elements of a 350 mg total weight gastro-erosional granulation formulation tablet comprising 15 mg tetrabenazine.

TABLE 2

| Material | mg/tab | % |
|---|---|---|
| Tetrabenazine (milled) | 15.0 | 4.3 |
| Mannitol Powder | 185.4 | 53.0 |
| Microcrystalline Cellulose | 61.8 | 17.7 |
| PVP K29/32 | 14.0 | 4.0 |
| Tween 80 (Polysorbate 80) | 3.8 | 1.1 |
| Mannogem EZ (spray dried mannitol) | 31.5 | 9.0 |
| POLYOX ® N60K | 35.0 | 10.0 |
| Magnesium Stearate | 3.5 | 1.0 |
| Totals: | 350.0 | 100.0 |

Same process as described for Example 1.

Example 3

15 mg Tetrabenazine Gastro-Retentive Extended Release (Large Tablet) (Formulation B)

Figure 2:
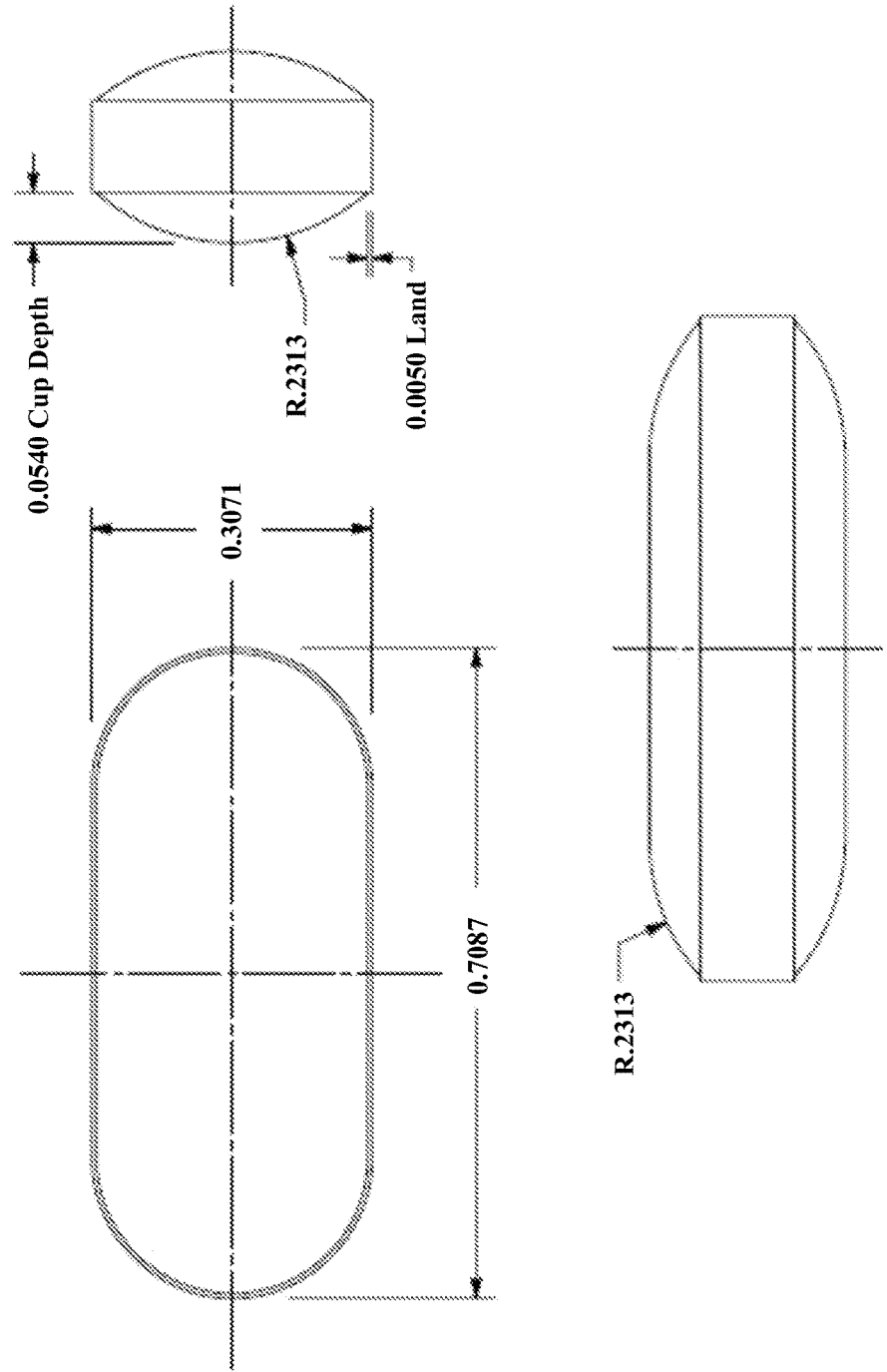
FIG. 2: Dimensions of Gastro-Retentive Extended Release Large Tablet.

Table 3 below discloses the elements of a 700 mg total weight gastro-retentive formulation tablet comprising 15 mg tetrabenazine. The gastro-retentive tablet is an elongated capsule having dimensions of approximately 0.7087 in. long by 0.3071 in. wide, having rounded ends with a cup depth of 0.0540 in. on each opposing side, as shown in FIG. 2.

TABLE 3

| Material | mg/tab | % |
|---|---|---|
| Tetrabenazine (milled) | 15.0 | 2.1 |
| Mannitol Powder | 357.5 | 51.1 |
| Microcrystalline Cellulose | 119.0 | 17.0 |
| PVP K29/32 | 26.0 | 3.7 |
| Tween 80 (Polysorbate 80) | 7.5 | 1.1 |
| Mannogem EZ (spray dried mannitol) | 28.0 | 4.0 |
| POLYOX ® N60K | 140.0 | 20.0 |
| Magnesium Stearate | 7.0 | 1.0 |
| Totals: | 700.0 | 100.0 |

Same Process as described for Example 1. But theoretical compression weight is 700 mg.

Example 4

15 mg Tetrabenazine Gastro-Retentive Extended Release (Large Tablet) (Formulation B)

Table 4 below discloses the elements of a 700 mg total weight gastro-retentive formulation tablet comprising 15 mg tetrabenazine. The gastro-retentive tablet is an elongated capsule having dimensions of approximately 0.7087 in. long by 0.3071 in. wide, having rounded ends with a cup depth of 0.0540 in. on each opposing side, as shown in FIG. 2.

TABLE 4

| Material | mg/tab | % |
|---|---|---|
| Tetrabenazine (milled) | 15.0 | 2.1 |
| Mannitol Powder | 357.5 | 51.1 |
| Microcrystalline Cellulose | 119.0 | 17.0 |
| PVP K29/32 | 26.0 | 3.7 |
| Tween 80 (Polysorbate 80) | 7.5 | 1.1 |
| Mannogem ® EZ (spray dried mannitol) | 45.5 | 6.5 |
| POLYOX ® N60K | 122.5 | 17.5 |
| Magnesium Stearate | 7.0 | 1.0 |
| Totals: | 700.0 | 100.0 |

Same Process as described for Example 1. But theoretical compression weight is 700 mg.

Example 5

6 mg Tetrabenazine Immediate Release Tablet

Table 5 below discloses the elements of a 125 mg total weight immediate-release tablet comprising 6 mg tetrabenazine.

TABLE 5

| Material | mg/tab | % |
|---|---|---|
| Tetrabenazine (milled) | 6.0 | 4.8 |
| Mannitol Powder | 75.0 | 60.0 |
| Microcrystalline Cellulose | 25.0 | 20.0 |
| Sodium Starch Glycolate | 2.5 | 2.0 |
| PVP K29/32 | 6.0 | 4.8 |
| Tween 80 (Polysorbate 80) | 1.0 | 0.8 |
| Mannogem ® EZ (spray dried mannitol) | 5.8 | 4.6 |
| Sodium Starch Glycolate | 2.5 | 2.0 |
| Magnesium Stearate | 1.2 | 1.0 |
| Totals: | 125.0 | 100.0 |

Tetrabenazine (milled) is combined along with Mannitol Powder, Microcrystalline Cellulose, Sodium Starch Glycolate, PVP K29/32 and Tween 80 (Polysorbate 80) into a high shear granulator and initially dry mixed at high impeller and chopper speed for 5 minutes. While mixing at high impeller speed and low chopper speed, Purified Water is added to the mixing powders to granulate the material. Additional mixing and water addition with high impeller and high chopper speed continues until the desired granulation end-point is achieved. The resulting granulation is wet screened to break up any oversized agglomerates and the material is added to a fluid bed drier and dried at 60° C. until the desired L.O.D. (loss on drying) is achieved. The dried material is sieved through a #20 mesh screen and the oversized material is milled to a particle size of just under 20 mesh in size. The dried and sized material is combined with Spray Dried Mannitol and Sodium Starch Glycolate into a diffusive mixer (V-Blender) where it is blended for 15 minutes. Magnesium Stearate is then passed through a #30 mesh screen and added to the blended material in the V-Blender. The contents are then lubricated for 3 minutes and discharged for tablet compression. Using a rotary tablet press fitted with punches and dies of the desired shape and size, the lubricated blend is compressed into tablets of a theoretical weight of 125 mg.

Examples 6-8

6 mg, 12 mg, and 18 mg Tetrabenazine Gastro-Erosional Extended Release (Small Tablet)

Table 6 discloses additional strengths of the sustained release 350 mg tablet formulation containing anti-oxidants and an aqueous film coating.

TABLE 6

| Material | mg/tab | % | mg/tab | % | mg/tab | % |
|---|---|---|---|---|---|---|
| Tetrabenazine (milled) | 6.0 | 1.7 | 12.0 | 3.4 | 18.0 | 5.1 |
| Mannitol Powder | 191.3 | 54.7 | 186.9 | 53.4 | 180.5 | 51.6 |
| Microcrystalline Cellulose | 64.2 | 18.3 | 62.6 | 17.9 | 63.0 | 18.0 |
| PVP K29/32 | 14.0 | 4.0 | 14.0 | 4.0 | 14.0 | 4.0 |
| BHA | 0.5 | 0.1 | 0.5 | 0.1 | 0.5 | 0.1 |
| Tween 80 (Polysorbate 80) | 4.0 | 1.1 | 4.0 | 1.1 | 4.0 | 1.1 |
| Mannogem ® EZ (spray dried mannitol) | 31.1 | 8.9 | 31.1 | 8.9 | 31.1 | 8.9 |
| POLYOX ® N60K | 35.0 | 10.0 | 35.0 | 10.0 | 35.0 | 10.0 |
| BHT | 0.4 | 0.1 | 0.4 | 0.1 | 0.4 | 0.1 |
| Magnesium Stearate | 3.5 | 1.0 | 3.5 | 1.0 | 3.5 | 1.0 |
| Totals: | 350.0 | 100.0 | 350.0 | 100.0 | 350.0 | 100.0 |
| Core Tablets: | 350.0 | 97.1 | 350.0 | 97.1 | 350.0 | 97.1 |
| Opadry II 85F184 22 White | 10.5 | 2.9 | 10.5 | 2.9 | 10.5 | 2.9 |
| Totals (Coated Tablets): | 360.5 | 100.0 | 360.5 | 100.0 | 360.5 | 100.0 |

Tetrabenazine (milled) is combined along with Mannitol Powder, Microcrystalline Cellulose, PVP K29/32, BHA and Tween 80 (Polysorbate 80) into a high shear granulator and initially dry mixed at high impeller and chopper speed for 5 minutes. While mixing at high impeller speed and low chopper speed, Purified Water is added to the mixing powders to granulate the material. Additional mixing and water addition with high impeller and high chopper speed continues until the desired granulation end-point is achieved. The resulting granulation is wet screened to break up any oversized agglomerates and the material is added to a fluid bed drier and dried at 60° C. until the desired L.O.D. (loss on drying) is achieved. The dried material is sieved through a #20 mesh screen and the oversized material is milled to a particle size of just under 20 mesh in size. The dried and sized material is combined with Spray Dried Mannitol, BHT and POLYOX® N60K into a diffusive mixer (V-Blender) where it is blended for 15 minutes. Magnesium Stearate is then passed through a #30 mesh screen and added to the blended material in the V-Blender. The contents are then lubricated for 3 minutes and discharged for tablet compression. Using a rotary tablet press fitted with punches and dies of the desired shape and size, the lubricated blend is compressed into tablets of a theoretical weight of 350 mg. The tablet cores are then placed into a side vented, fully perforated coating pan where they are coated with a 20% solids dispersion of Opadry® II 85F18422 White in Water until a theoretical weight gain of 3% is obtained.

The following examples may be made with varying amounts of tetrabenazine, and increasing proportionally the amount of filler material. Those skilled in the art will easily be able to vary the proportions of glidants, fillers/diluents, binders, disintegrants, and other ingredients in order to optimize the formulation and its method of manufacture.

Example 9

8 mg and 15 mg Tetrabenazine Gastro-Erosional Extended Release (Small Tablet)

Table 7 below discloses the elements of a 350 mg total weight gastro-erosional granulation formulation tablet comprising 8 mg or 15 mg tetrabenazine, as well as optionally coated 360.5 mg total weight gastro-erosional granulation formulation tablet comprising 8 mg or 15 mg tetrabenazine.

TABLE 7

| Material | mg/tab | % | mg/tab | % |
|---|---|---|---|---|
| Tetrabenazine (milled) | 8.0 | 2.3 | 15.0 | 4.3 |
| Sodium Ascorbate | 5.0 | 1.4 | 5.0 | 1.4 |
| Mannitol Powder | 186.9 | 53.4 | 181.7 | 51.9 |
| Microcrystalline Cellulose | 62.3 | 17.8 | 60.6 | 17.3 |
| PVP K29/32 | 14.0 | 4.0 | 14.0 | 4.0 |
| Tween 80 (Polysorbate 80) | 3.8 | 1.1 | 3.8 | 1.1 |
| Mannogem ® EZ (spray dried mannitol) | 31.5 | 9.0 | 31.5 | 9.0 |
| Kollidon SR | 35.0 | 10.0 | 35.0 | 10.0 |
| Magnesium Stearate | 3.5 | 1.0 | 3.5 | 1.0 |
| Totals: | 350.0 | 100.0 | 350.0 | 100.0 |
| Core Tablets: | 350.0 | 97.1 | 350.0 | 97.1 |
| Opadry II 85F184 22 White | 10.5 | 2.9 | 10.5 | 2.9 |
| Totals (Coated Tablets): | 360.5 | 100.0 | 360.5 | 100.0 |

Same process as described for Example 1.

From the foregoing description, one skilled in the art can ascertain the essential characteristics of this invention, and without departing from the spirit and scope thereof, can make various changes and modifications of the invention to adapt it to various usages and conditions.

What is claimed is:

1. An extended-release pharmaceutical formulation comprising, in a solid dosage form for oral delivery of between about 100 mg and about 1 g total weight:
   between about 2 and about 18% of an active ingredient that is tetrabenazine;
   between about 70% and about 96% of one or more diluents selected from the group consisting of mannitol powder, spray dried mannitol, microcrystalline cellulose, lactose, dicalcium phosphate, tricalcium phosphate, starch, pregelatinized starch, compressible sugars, silicified microcrystalline cellulose, and calcium carbonate;
   between about 1% and about 10% of a water-soluble binder selected from the group consisting of polyvinylpyrrolidone, hydroxypropylcellulose (HPC), hydroxypropylmethylcellulose (HPMC), ethylcellulose (EC), corn starch, pregelatinized starch, gelatin, and sugar; and
   between about 0.5 and about 2% of a surfactant selected from the group consisting of polysorbate, sodium lauryl sulfate, and docusate sodium.

2. The extended-release pharmaceutical formulation of claim 1, wherein:
   the diluent is mannitol, lactose, or microcrystalline cellulose;
   the binder is a polyvinylpyrrolidone; and
   the surfactant is a polysorbate.

3. The extended-release pharmaceutical formulation of claim 1 comprising between about 2.5% and about 11% of the active ingredient.

4. The extended-release pharmaceutical formulation of claim 1, comprising:
   between about 60% and about 70% of mannitol or lactose;
   between about 15% and about 25% of microcrystalline cellulose;
   about 5% of polyvinylpyrrolidone; and
   between about 1 and about 2% of polysorbate 80.

5. An extended-release pharmaceutical formulation comprising, in a solid dosage form for oral delivery of between about 100 mg and about 1 g total weight:
   between about 70 and about 95% of a granulation of an active ingredient that is tetrabenazine, wherein the active ingredient comprises between about 1% and about 15% of the granulation;
   between about 5% and about 15% of one or more diluents;
   between about 5% and about 20% of a sustained-release polymer; and
   between about 0.5 and about 2% of a lubricant.

6. The extended-release pharmaceutical formulation of claim 5 comprising:
   between about 5% and about 15% of one or more spray-dried mannitol or spray-dried lactose;
   between about 5% and about 20% of a sustained-release polymer; and
   between about 0.5 and about 2% of a magnesium stearate.

7. The extended-release pharmaceutical formulation of claim 5, wherein the sustained-release polymer is a polyvinyl acetate-polyvinylpyrrolidone mixture.

8. The extended-release pharmaceutical formulation of claim 5, wherein the sustained-release polymer is a poly(ethylene oxide) polymer.

9. The extended-release pharmaceutical formulation of claim 5, wherein the extended-release pharmaceutical formulation comprises from about 5 mg to about 250 mg of the active ingredient.

10. A method of alleviating or abrogating a VMAT-mediated disease, comprising administering to a subject in need thereof the extended release pharmaceutical composition as recited in claim 1, wherein the dose-normalized $C_{max}$ of the active ingredient resulting from the administration of the extended-release pharmaceutical formulation is lower than the dose-normalized $C_{max}$ resulting from the administration of the immediate release formulated or unformulated active ingredient.

11. The method of claim 10, wherein the ratio of extended release formulated $C_{max}$ to immediate release formulated or unformulated $C_{max}$ is less than 1.

12. A method of alleviating or abrogating a VMAT2-mediated disease, comprising administering to a subject in need thereof the extended release pharmaceutical composition as recited in claim 1, wherein the $T_{max}$ of the active ingredient resulting from the administration of the extended-release pharmaceutical formulation occurs later than the $T_{max}$ resulting from the administration of the immediate release formulated or unformulated active ingredient.

13. The method of claim 12, wherein the ratio of immediate release formulated or unformulated $T_{max}$ to extended release formulated $T_{max}$ is less than 1.

14. A method of alleviating or abrogating a VMAT-mediated disease, comprising administering to a subject in need thereof the extended release pharmaceutical composition as recited in claim 1, wherein the extended release pharmaceutical composition is administered with food and the ratio of fed to fasted $C_{max}$ of the total combined amount of the active ingredient is greater than 1.

15. A method of alleviating or abrogating a VMAT-mediated disease, comprising administering to a subject in need thereof the extended release pharmaceutical composition as recited in claim 1, wherein the ratio of fed to fasted $AUC_{inf}$ of the active ingredient is greater than 1.

16. A method of alleviating or abrogating a VMAT2-mediated disease, comprising administering to a subject the extended release pharmaceutical composition as recited in claim 1, wherein the composition is administered with food and the ratio of fed to fasted $AUC_t$ of the active ingredient is greater than 1.

17. The method as recited in claim 15, wherein the ratio of fed to fasted $AUC_{inf}$ of the active ingredient is greater than 1 and the $T_{max}$ of dihydrotetrabenazine resulting from the administration of the extended-release pharmaceutical formulation occurs later than the $T_{max}$ resulting from the administration of immediate release formulated or unformulated tetrabenazine.

18. The method of claim 17, wherein the ratio of immediate release formulated or unformulated $T_{max}$ to extended release formulated $T_{max}$ is less than 1.

19. The method as recited in claim 15, wherein the composition is administered with food, the ratio of fed to fasted $AUC_{inf}$ of the active ingredient is greater than 1, and the ratio of fed to fasted $C_{max}$ of the total combined amount of dihydrotetrabenazine is greater than 1.

20. The method as recited in claim 15, wherein the composition is administered with food, the ratio of fed to fasted $AUC_{inf}$ of the active ingredient is greater than 1, and the ratio of fed to fasted $AUC_{inf}$ of the total combined amount of dihydrotetrabenazine is greater than 1.

21. The method as recited in claim 15, wherein the composition is administered with food, the ratio of fed to fasted $AUC_{inf}$ of the active ingredient is greater than 1, and the ratio of fed to fasted $AUC_t$ of the total combined amount of dihydrotetrabenazine is greater than 1.

* * * * *